United States Patent
Packiarajan

(10) Patent No.: US 6,936,607 B2
(45) Date of Patent: Aug. 30, 2005

(54) 2,4,6-TRIAMINOPYRIMIDINES FOR THE TREATMENT OF DEPRESSION AND/OR ANXIETY

(75) Inventor: Mathivanan Packiarajan, Saddle Brook, NJ (US)

(73) Assignee: H. Lunobeck A/S, Valby-Copenhagen (DK)

(*) Notice: Subject to any disclaimer, the term of this patent is extended or adjusted under 35 U.S.C. 154(b) by 0 days.

(21) Appl. No.: 10/638,602

(22) Filed: Aug. 7, 2003

(65) Prior Publication Data

US 2004/0082587 A1 Apr. 29, 2004

Related U.S. Application Data

(60) Provisional application No. 60/401,939, filed on Aug. 7, 2002.

(51) Int. Cl.$^7$ .............................................. A61K 31/535
(52) U.S. Cl. .............................. 514/235.8; 514/252.14; 514/275; 544/122; 544/296; 544/323
(58) Field of Search ................................ 544/122, 296, 544/323; 514/235.8, 252.14, 275

(56) References Cited

U.S. PATENT DOCUMENTS

| | | | |
|---|---|---|---|
| 4,946,956 A | 8/1990 | Wheeler et al. | |
| 5,017,466 A | 5/1991 | Kobayashi et al. | |
| 2003/0078271 A1 * | 4/2003 | Blackburn et al. | 514/252.14 |
| 2004/0127502 A1 | 7/2004 | Blackburn et al. | |

FOREIGN PATENT DOCUMENTS

| | | |
|---|---|---|
| GB | 1477349 | 6/1977 |
| JP | 11-158073 | 6/1999 |
| WO | WO02060392 | 8/2002 |

OTHER PUBLICATIONS

Kinney et al., Galanin Receptor–Mediated Inhibition of Glutamate Release in the Arcuate Nucleus of the Hypothalamus, The Journal of Neuroscience, May 15, 1998, 18(10: 3489–3500.*

* cited by examiner

Primary Examiner—Deepak Rao
(74) Attorney, Agent, or Firm—Stephen G. Kalinchak

(57) ABSTRACT

This invention is directed to pyrimidine derivatives which are selective antagonists for the GalR3 receptor. The invention provides a pharmaceutical composition comprising a therapeutically effective amount of a compound of the invention and a pharmaceutically acceptable carrier. This invention also provides a pharmaceutical composition made by combining a therapeutically effective amount of a compound of the invention and a pharmaceutically acceptable carrier. This invention further provides a process for making a pharmaceutical composition comprising combining a therapeutically effective amount of a compound of the invention and a pharmaceutically acceptable carrier. This invention also provides a method of treating a subject suffering from depression and/or anxiety which comprises administering to the subject an amount of a compound of the invention effective to treat the subject's depression and/or anxiety. This invention also provides a method of treating depression and/or anxiety in a subject which comprises administering to the subject a composition comprising a pharmaceutically acceptable carrier and a therapeutically effective amount of a GalR3 receptor antagonist.

25 Claims, No Drawings

2,4,6-TRIAMINOPYRIMIDINES FOR THE TREATMENT OF DEPRESSION AND/OR ANXIETY

This application claims priority of U.S. Provisional Application No. 60/401,939, filed Aug. 7, 2002, the contents of which are hereby incorporated by reference.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to describe more fully the art to which this invention pertains.

Depression is the most common of mental disorders and yet is often underdiagnosed and undertreated, inflicting substantial morbidity and psychosocial impairment on its sufferers. Depression is mainly characterized by sadness, flatness, loss of feeling, anhedonia (lack of pleasure), tearfulness, agitation or retardation, thoughts of guilt and worthlessness; in severe cases, suicide, hallucinations and delusions.

Depression can be mainly categorized into bipolar disorders, identifying wide swings of mood; major depressive illness, marked by severe depressive symptoms but without manic swings; and less defined milder forms of bipolar disorder and major depression that fall short of the specific diagnostic criteria, e.g. dysthymic disorder (formerly called depressive neurosis). The symptomatology and diagnostic criteria for depression are set out in the Diagnostic and Statistical Manual of Mental Disorders, 4$^{th}$ edition (DSM IV; American Psychiatric Association, 1994a). Although many patients have single episodes of major depressive illness, the condition also can be repetitive, and this recurrent condition is frequently called unipolar depressive illness.

The key features of depressive illness are a markedly gloomy mood in which there is a loss of interest in life, and general feelings of hopelessness and worthlessness. Depressive symptoms range in severity from mild mood swings to severe delusions about self-worth, accomplishments, and the future.

The "blackness" of the presentation in the depressed patient is most often accompanied by severe motor retardation with profound sleep and appetite disturbance and suicidal ideation. Furthermore, depressive illness can also present in a highly anxious or agitated state.

The degree to which the underlying brain mechanisms in anxiety and depression differ or overlap remains unknown. The fact, however, that to some extent the same neurotransmitter systems are involved in depression and anxiety does not mean that the mechanisms are identical. However, the majority of people in an episode of either depression or anxiety also meet criteria for at least one other psychiatric disorder. But by far the strongest comorbidities in both cases are between depression and anxiety disorders. Therefore, it is now becoming common clinical practice to treat both indications with antidepressants such as selective serotonin re-uptake inhibitors.

The key clinical features of anxiety disorders relate to various combinations of psychological and physical manifestations of anxiety, not attributable to real danger and occurring either in attacks (panic disorder or PD) or as a persisting state (generalized anxiety disorder or GAD). Other neurotic features may be present (obsessional or hysterical symptoms) but do not dominate the clinical picture.

The Pathophysiology of Depression

Theories underlying the pathophysiology of depression have developed from several lines of evidence including: 1) changes in neurotransmitter monoamine levels; 2) endocrine imbalance; and 3) electrophysiological studies on sleep functions.

Evidence implicating the role of neurotransmitters in depression, in particular the monoamines serotonin, noradrenaline and dopamine, include the success of pharmacological agents in treating depressive disorders. Many of the tricylic antidepressants (TCAs), selective serotonin re-uptake inhibitors (SSRIs) and monoamine oxidase inhibitors (MAOIs) effective in the treatment of depression increase the availability of the catecholamines (noradrenaline and dopamine) and indolamines (serotonin) in the central nervous system (CNS). The clinical efficacy of these agents has given rise to the catecholamine-indolamine hypothesis of depression. This theory postulates that a certain level of amines and/or receptor sensitivity to catecholamines functions to generate a normal mood. A receptor insensitivity, a depletion of monoamines, or a decrease in their release, synthesis or storage have been postulated to lead to depression.

Current Treatments for Depression

A variety of pharmacological agents have been employed to treat depression based on the catecholamine-indolamine hypothesis of depression. Drugs used to treat depression include MAOIs, atypical antipsychotics, lithium, TCAs, and SSRIs. In addition, a number of off-label agents such as antiepileptics are used to treat depression in treatment-resistant patients.

Tricyclic antidepressants are about equal to SSRIs in effectiveness against depression, thus providing supporting evidence for the catecholamine-indolamine hypothesis of depression. However, SSRIs have largely displaced TCAs because of side effects associated with TCAs and the need to monitor EKG and plasma drug concentration. Although the SSRIs are viewed as an improvement over other antidepressants, they are not without their clinical problems. Adverse effects on sexual function, primarily anorgasmia and delayed ejaculation, have been consistently reported. Other, common side-effects include sleep disorders, yawning, weight changes, suicidal ideation and extrapyramidal-like side-effects such as dystonic reactions. Thus, there clearly remains a medical need for new treatments of depression, without the adverse side effect profile of existing agents and with improved efficacy.

Current Treatments For Anxiety

There is now considerable direct evidence for the efficacy of the SSRIs both in depression and in anxiety disorders.

Of the current SSRIs approved for marketing in the United States all have shown sufficient efficacy to be further approved for the treatment of at least one anxiety disorder, for example obsessive compulsive disorder (OCD) or generalized anxiety disorder (GAD). Compounds such as paroxetine and sertraline are also indicated for the treatment of panic disorder (PD).

However, it is clear from the issues raised earlier relating to the efficacy and side effect profile of SSRIs and for that matter the more widely prescribed benzodiazapines, there still exists a real medical need for novel approaches for the treatment of anxiety and depression.

Discovery Of GalR3 Receptor Subtype And Its Role In Depression and Anxiety

The investigations leading to the present invention were preceded by the discovery that mRNA for the GalR3 receptor is localized to areas of the rat brain associated with mood and emotion, thus supporting the expression of GalR3 in those regions. GalR3 receptor protein also localizes to areas of the rat brain associated with mood and emotion.

This discovery led to the concept that the GalR3 receptor plays a role in controlling the activity of catecholamine and indolamine neurons in the CNS. Galanin is known to hyperpolarize neurons, including monoaminergic neurons (Seutin, et al., 1989) and to have inhibitory effects on 5-HT neurons (Xu, et al., 1998), and dopamine neurons (Gopalan, et al., 1993; De Weille, et al., 1989; Jansson, et al., 1989; Nordstrom, et al., 1987; Weiss, et al., 1998). A series of in vivo behavioral experiments were carried out to evaluate the antidepressant and anxiolytic properties of a selective GalR3 receptor antagonist. which established that selective antagonists of GalR3 are useful for the treatment of depression and/or anxiety. We now report novel chemical structures that are high affinity antagonists of GalR3. By virtue of their ability to antagonize the GalR3 receptor, these compounds are useful for the treatment of depression and/or anxiety.

The Rat Forced Swim Test and the rat Social Interaction Test can be employed to evaluate the use of selective GalR3 receptor antagonists to treat depression and anxiety. These models are considered by experts in the field to be predictive of the potential utility of agents to treat depression and anxiety.

Rat Forced Swim Test (FST)

The rat Forced Swim Test (FST) is a behavioral test that is used to screen compounds for antidepressant efficacy (Porsolt et al., 1977, 1978; Porsolt, 1981). This test is widely used, relatively easy to perform, and sensitive to the effects of some of the major classes of antidepressant drugs, including TCAs and MAOIs, and various atypical antidepressants. Furthermore, this test is relatively selective for antidepressant drugs in the sense that few psychoactive drugs produce similar behavioral actions in the FST.

In the rat FST, animals are placed in a cylinder of water, from which there is no escape, for an extended period of time. Typically, animals will display a range of behaviors such as immobility, climbing, swimming, and diving, with immobility being predominant after several minutes of immersion in the water. Consequently, many past studies have only measured or scored immobility after the administration of the test agent. Unfortunately, this method does not score any other active behaviors that may be produced by potential antidepressants. Thus, if a particular class of antidepressant were to have very little effect on immobility, yet produce characteristic behaviors during the FST, these behaviors would not be scored and the conclusion would be that the compound in question does not possess antidepressant action.

Recently, however, a sampling technique was developed to score active behaviors in the FST, such as swimming, climbing and diving, in addition to immobility (Detke, et al., 1995; Lucki, 1997; Page, et al., 1999; Reneric and Lucki, 1998). This modified sampling technique has indicated that SSRIs, such as fluoxetine, paroxetine and sertraline, significantly decrease immobility and increase swimming time (Detke, et al., 1995; Page, et al., 1999). In contrast, selective reuptake inhibitors of norepinephrine (NE) increase climbing behavior but do not alter swimming time (Detke, et al., 1995; Page, et al., 1999).

Rat Social Interaction Test (SIT)

There are a number of paradigms that have been used to determine whether a compound possesses anxiolytic action. A number of these tests involve food or water deprivation, punishment or measurement of consummatory behavior (see File, et al., 1980; File, 1985; Rodgers, et al., 1997; and Treit, 1985, for review). In addition, in these models, prior conditioning reduces the uncertainty or anxiety. In general, these tests lack ethological validity.

One model that is based upon an unconditioned response that does not involve punishment or deprivation is the Social Interaction Test (SIT) (File and Hyde, 1978, 1979). In this model, rats previously housed singly are placed in a familiar, dimly lit, test arena with weight-matched, novel partners. The principal anxiogenic stimulus under these conditions is the partner novelty, which involves an unconditioned response to a potential threat. After pharmacological treatments, the following behaviors are scored as active social interaction: grooming, sniffing, biting, boxing, wrestling, following, crawling over and crawling under. A wide range of psychoactive drugs have been examined in this paradigm and it has been shown that the social interaction test can distinguish anxiolytics from antidepressants, antipsychotics, analeptics and sedative agents (File, 1985; Guy and Gardner, 1985). This test can detect anxiolytic agents such as the benzodiazepines (File and Hyde, 1978; File and Hyde, 1979; File, 1980), in addition to non-benzodiazepines, including paroxetine and other SSRIs (Lightowler, et al., 1994). Finally, the social interaction test can detect anxiogenic agents, including the inverse benzodiazepine receptor agonists (File, et al., 1982; File and Pellow, 1983; File and Pellow, 1984; File, 1985).

We now have unexpectedly discovered that the novel pyrimidines described herein are high affinity antagonists of GalR3, and useful, by virtue of their ability to antagonize the GalR3 receptor, for the treatment of depression and/or anxiety.

In an embodiment of the present invention the synthesis of pyrimidines which bind with high affinity to the cloned human GalR3 receptor is disclosed. Thus, the GalR3 receptor antagonists described herein, which may be further classified as neutral antagonists, inverse agonists or allosteric modulators, provide a novel method to treat depressive disorders and/or anxiety.

SUMMARY OF THE INVENTION

This invention provides a compound having the structure:

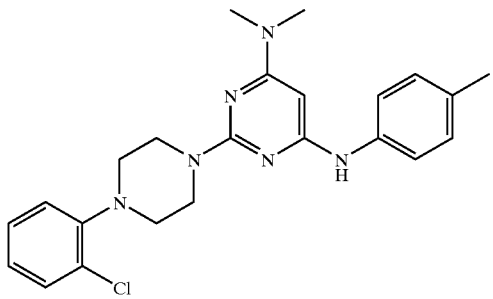

This invention provides a compound having the structure:

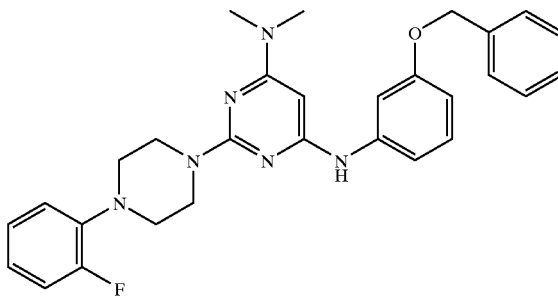

This invention provides a compound having the structure:

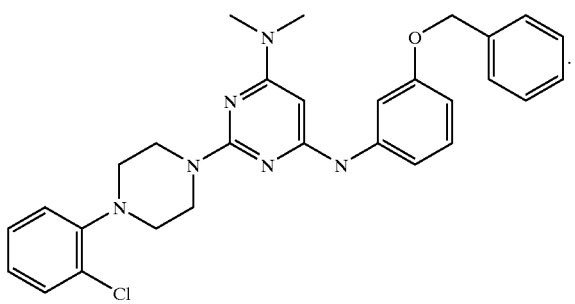

This invention provides a compound having the structure:

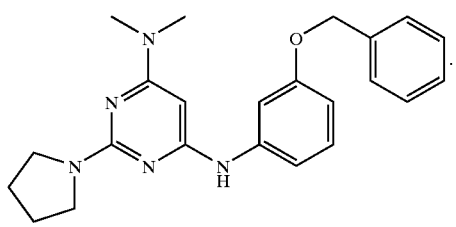

This invention provides a compound having the structure:

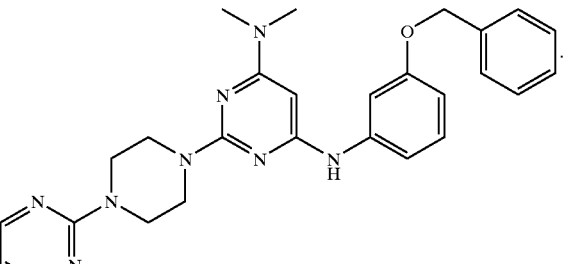

This invention provides a compound having the structure:

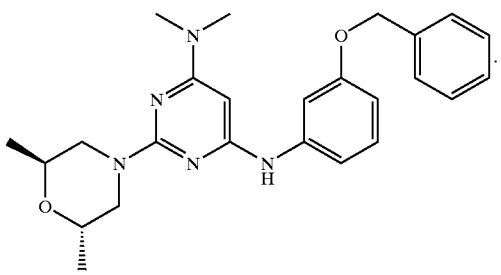

This invention also provides a pharmaceutical composition comprising a therapeutically effective amount of the compound of this invention and a pharmaceutically acceptable carrier.

This invention provides a process for making a pharmaceutical composition comprising admixing a therapeutically effective amount of the compound of this invention and a pharmaceutically acceptable carrier.

The present invention provides for the use of any of the chemical compounds of the invention for the preparation of a pharmaceutical composition for treating an abnormality. The invention also provides for the use of any of the chemical compounds of the invention for the preparation of a pharmaceutical composition for treating an abnormality, wherein the abnormality is alleviated by decreasing the activity of a human GalR3 receptor. In one embodiment, the abnormality is depression. In one embodiment, the abnormality is anxiety.

The present invention provides for a method of treating a subject suffering from depression which comprises administering to the subject an amount of any of the compounds of the invention effective to treat the subject's depression.

The invention also provides a method of treating anxiety in a subject which comprises administering to the subject an amount of any of the compounds of the invention effective to treat the subject's anxiety.

DETAILED DESCRIPTION OF THE INVENTION

This invention provides a compound having the structure:

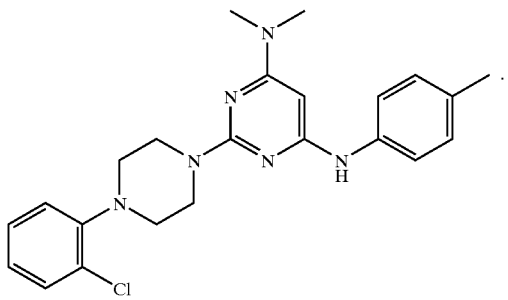

This invention provides a compound having the structure:

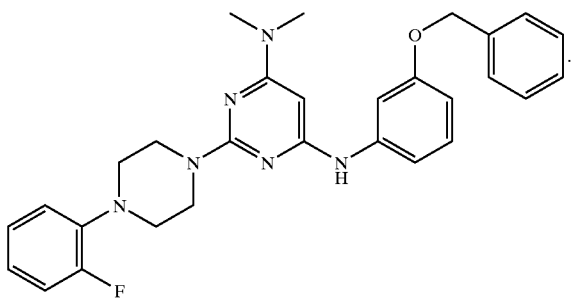

This invention provides a compound having the structure:

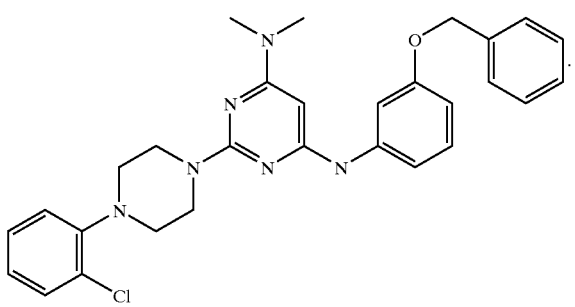

This invention provides a compound having the structure:

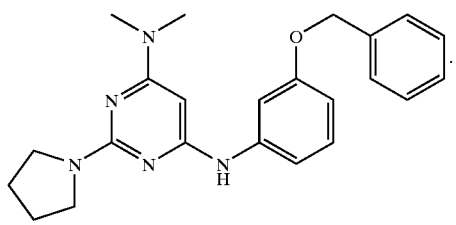

This invention provides a compound having the structure:

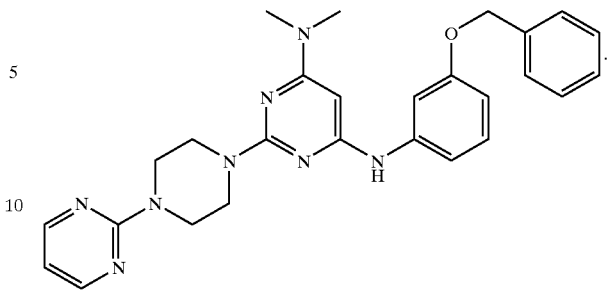

This invention provides a compound having the structure:

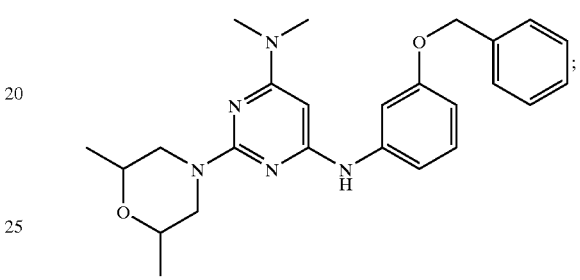

wherein the methyl groups off the morpholine are trans to each other.

In one embodiment, the compound is enantiomerically pure.

In one embodiment, the compound is diastereomerically pure.

In one embodiment, the compound is enantiomerically and diastereomerically pure.

In the present invention the term "aryl" is phenyl or naphthyl. The term "aryl" also includes phenyl and naphthyl which may be substituted with one or more of the following: —F, —Cl, —Br, —I, —NO$_2$, —CN, straight chained or branched $C_1$–$C_7$ alkyl, monofluoroalkyl or polyfluoroalkyl, straight chained or branched $C_2$–$C_7$ alkenyl or alkynyl, $C_3$–$C_7$ cycloalkyl, monofluorocycloalkyl or polyfluorocycloalkyl or $C_5$–$C_7$ cycloalkenyl.

The invention provides for each pure stereoisomer of any of the compounds described herein. Such stereoisomers may include enantiomers and diastereomers. The invention also provides for stereoisomeric mixtures, including racemic mixtures or diastereomeric mixtures. Stereoisomers can be synthesized in pure form (Nógrádi, M. 1987 and Asymmetric Synthesis 1983) or they can be resolved by a variety of methods such as crystallization and chromatographic techniques (Jaques, J. et al. 1981, and Asymmetric Synthesis 1983).

The compounds of the present invention are preferably greater than 80% pure, more preferably greater than 90% pure, and most preferably greater than 95% pure.

Included in this invention are pharmaceutically acceptable salts and complexes of all of the compounds described herein. The acids and bases from which these salts are prepared include but are not limited to the acids listed herein. The acids include, but are not limited to, the following inorganic acids: hydrochloric acid, hydrobromic acid, hydroiodic acid, sulfuric acid and boric acid. The acids include, but are not limited to, the following organic acids: acetic acid, malonic acid, succinic acid, fumaric acid, tartaric acid, maleic acid, citric acid, methanesulfonic acid, benzoic acid, glycolic acid, lactic acid and mandelic acid. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, 1985.

The present invention further includes metabolites of the compounds of the present invention. Metabolites include active species produced upon introduction of compounds of this invention into the biological milieu.

This invention also provides a pharmaceutical composition comprising a therapeutically effective amount of the compound of this invention and a pharmaceutically acceptable carrier.

This invention provides a process for making a pharmaceutical composition comprising admixing a therapeutically effective amount of the compound of this invention and a pharmaceutically acceptable carrier.

The present invention provides for the use of any of the chemical compounds of the invention for the preparation of a pharmaceutical composition for treating an abnormality. The invention also provides for the use of any of the chemical compounds of the invention for the preparation of a pharmaceutical composition for treating an abnormality, wherein the abnormality is alleviated by decreasing the activity of a human GalR3 receptor. In one embodiment, the abnormality is depression. In one embodiment, the abnormality is anxiety. In one embodiment, the abnormality is major depressive disorder. In one embodiment, the abnormality is obsessive compulsive disorder. In one embodiment, the abnormality is panic disorder, with or without agoraphobia. In one embodiment, the abnormality is social anxiety disorder. In one embodiment, the abnormality is generalized anxiety disorder. In one embodiment, the abnormality is post-traumatic stress disorder.

In one embodiment, the amount of the compound is from about 0.01 mg to about 1000 mg. In another embodiment, the amount of the compound is from about 0.01 mg to about 500 mg. In yet another embodiment, the amount of the compound is from about 0.1 mg to about 500 mg. In another embodiment, the amount of the compound is from about 1.0 mg to about 200 mg. In yet another embodiment, the amount of the compound is from about 10 mg to about 100 mg.

In a further embodiment, the carrier is a liquid and the composition is a solution. In another embodiment, the carrier is a solid and the composition is a tablet. In another embodiment, the carrier is a gel and the composition is a capsule, suppository or a cream. In a further embodiment the compound may be formulated as a part of a pharmaceutically acceptable transdermal patch. In yet a further embodiment, the compound may be delivered to the subject by means of a spray or inhalant.

A solid carrier can include one or more substances which may also act as endogenous carriers (e.g. nutrient or micronutrient carriers), flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, coloring agents, viscosity regulators, stabilizers or osmoregulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate or isopropyl myristate. Sterile liquid carriers are useful in sterile liquid form compositions for parenteral administration. The liquid carrier for pressurized compositions can be a halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. In one embodiment, the compound is administered in combination with food. Forms useful for parenteral administration include sterile solutions, emulsions, and suspensions.

The following description of depressive and anxiety disorders is provided for the purpose of facilitating an understanding of the utility of the compounds of this invention. The definitions of depressive and anxiety disorders given below are those listed in American Psychiatric Association, 1994a or American Psychiatric Association, 1987. Additional information regarding these disorders can be found in this reference, as well as other references cited below, all of which are hereby incorporated herein by reference.

Depressive disorders include major depressive disorder and dysthymic disorder (American Psychiatric Association, 1994a; American Psychiatric Association, 1994b). Major depressive disorder is characterized by the occurrence of one or more major depressive episodes without manic or hypomanic episodes. A major depressive episode is defined as a prominent and relatively persistent depressed or dysphoric mood that usually interferes with daily functioning (nearly every day for at least 2 weeks); it should include at least 4 of the following 8 symptoms: change in appetite, change in sleep, psychomotor agitation or retardation, loss of interest in usual activities or decrease in sexual drive, increased fatigue, feelings of guilt or worthlessness, slowed thinking or impaired concentration, and a suicide attempt or suicidal ideation. Dysthymic disorder involves a type of depression that is not severe enough to be called a major depressive episode, but that lasts much longer than major depressive disorder, without high phases.

It is contemplated that the compounds of this invention will be effective in treating depression in patients who have been diagnosed as having depression based upon the administration of any of the following tests: Hamilton Depression Rating Scale (HDRS), Hamilton depressed mood item, Clinical Global Impressions (CGI)-Severity of Illness. It is further contemplated that the compounds of the invention will be effective in inducing improvements in certain of the factors measured in these tests, such as the HDRS subfactor scores, including the depressed mood item, sleep disturbance factor and anxiety factor, and the CGI-Severity of Illness rating. It is also contemplated that the compounds of this invention will be effective in preventing relapse of major depressive episodes.

The present invention provides for a method of treating a subject suffering from depression which comprises administering to the subject an amount of any of the compounds of the invention effective to treat the subject's depression.

The invention provides a method of treating a subject suffering from major depressive disorder, which comprises administering to the subject an amount of any of the compounds of the invention effective to treat the subject's major depressive disorder.

Anxiety disorders include panic disorder, agoraphobia with or without history of panic disorder, specific phobia, social phobia, obsessive-compulsive disorder, post-traumatic stress disorder, acute stress disorder and generalized anxiety disorder. It is contemplated that the compounds of this invention will be effective in treating these disorders in patients who have been diagnosed as having such disorders.

The present invention provides for a method of treating a subject suffering from anxiety which comprises administering to the subject an amount of any of the compounds of the invention effective to treat the subject's anxiety.

Obsessive compulsive disorder is characterized by recurrent and persistent ideas, thoughts, impulses or images (obsessions) that are ego-dystonic and/or repetitive, purposeful and intentional behaviors (compulsions) that are recognized by the person as excessive or unreasonable (American Psychiatric Association, 1994a). The obsessions or compulsions cause marked distress, are time-consuming, and/or significantly interfere with social or occupational functioning.

It is contemplated that the compounds of this invention will be effective in treating obsessions and compulsions in patients who have been diagnosed as having obsessive compulsive disorder based upon administration of appropriate tests, which may include, but are not limited to any of the following: Yale Brown Obsessive Compulsive Scale (YBOCS) (for adults), National Institute of Mental Health Global OCD Scale (NIMH GOCS), CGI-Severity of Illness scale. It is further contemplated that the compounds of the invention will be effective in inducing improvements in certain of the factors measured in these tests, such as a reduction of several points in the YBOCS total score. It is also contemplated that the compounds of this invention will be effective in preventing relapse of obsessive compulsive disorder.

The invention provides a method of treating obsessions and compulsions in a subject with obsessive compulsive disorder, which comprises administering to the subject an amount of any of the compounds of the invention effective to treat the subject's obsessions and compulsions.

Panic disorder is characterized by recurrent unexpected panic attacks and associated concern about having additional attacks, worry about the implications or consequences of the attacks, and/or a significant change in behavior related to the attacks (American Psychiatric Association, 1994a). A panic attack is defined as a discrete period of intense fear or discomfort in which four (or more) of the following symptoms develop abruptly and reach a peak within 10 minutes: (1) palpitations, pounding heart, or accelerated heart rate; (2) sweating; (3) trembling or shaking; (4) sensations of shortness of breath or smothering; (5) feeling of choking; (6) chest pain or discomfort; (7) nausea or abdominal distress; (8) feeling dizzy, unsteady, lightheaded, or faint; (9) derealization (feelings of unreality) or depersonalization (being detached from oneself); fear of losing control; (11) fear of dying; (12) paresthesias (numbness or tingling sensations); (13) chills or hot flushes. Panic disorder may or may not be associated with agoraphobia, or an irrational and often disabling fear of being out in public.

It is contemplated that the compounds of this invention will be effective in treating panic disorder in patients who have been diagnosed with panic disorder on the basis of frequency of occurrence of panic attacks, or by means of the CGI-Severity of Illness scale. It is further contemplated that the compounds of the invention will be effective in inducing improvements in certain of the factors measured in these evaluations, such as a reduction in frequency or elimination of panic attacks, an improvement in the CGI-Severity of Illness scale or a CGI-Global Improvement score of 1 (very much improved), 2 (much improved) or 3 (minimally improved). It is also contemplated that the compounds of this invention will be effective in-preventing relapse of panic disorder.

The invention provides a method of treating panic disorder, with or without agoraphobia, in a subject, which comprises administering to the subject an amount of any of the compounds of the invention effective to treat the subject's panic disorder.

Social anxiety disorder, also known as social phobia, is characterized by a marked and persistent fear of one or more social or performance situations in which the person is exposed to unfamiliar people or to possible scrutiny by others (American Psychiatric Association, 1994a). Exposure to the feared situation almost invariably provokes anxiety, which may approach the intensity of a panic attack. The feared situations are avoided or endured with intense anxiety or distress. The avoidance, anxious anticipation, or distress in the feared situation(s) interferes significantly with the person's normal routine, occupational or academic functioning, or social activities or relationships, or there is marked distress about having the phobias. Lesser degrees of performance anxiety or shyness generally do not require psychopharmacological treatment.

It is contemplated that the compounds of this invention will be effective in treating social anxiety disorder in patients who have been diagnosed as having social anxiety disorder based upon the administration of any of the following tests: the Liebowitz Social Anxiety Scale (LSAS), the CGI-Severity of Illness scale, the Hamilton Rating Scale for Anxiety (HAM-A), the Hamilton Rating Scale for Depression (HAM-D), the axis V Social and Occupational Functioning Assessment Scale of DSM-IV, the axis II (ICD-10) World Health Organization Disability Assessment, Schedule 2 (DAS-2), the Sheehan Disability Scales, the Schneier Disability Profile, the World Health Organization Quality of Life-100 (WHOQOL-100), or other tests as described in Bobes, 1998, which is incorporated herein by reference. It is further contemplated that the compounds of the invention will be effective in inducing improvements as measured by these tests, such as the a change from baseline in the Liebowitz Social Anxiety Scale (LSAS), or a CGI-Global Improvement score of 1 (very much improved), 2 (much improved) or 3 (minimally improved). It is also contemplated that the compounds of this invention will be effective in preventing relapse of social anxiety disorder.

The invention provides a method of treating social anxiety disorder in a subject which comprises administering to the subject an amount of any of the compounds of the invention effective to treat the subject's social anxiety disorder.

Generalized anxiety disorder is characterized by excessive anxiety and worry (apprehensive expectation) that is persistent for at least 6 months and which the person finds difficult to control (American Psychiatric Association, 1994a). It must be associated with at least 3 of the following 6 symptoms: restlessness or feeling keyed up or on edge, being easily fatigued, difficulty concentrating or mind going blank, irritability, muscle tension, sleep disturbance. The diagnostic criteria for this disorder are described in further detail in DSM-IV, which is incorporated herein by reference (American Psychiatric Association, 1994a).

It is contemplated that the compounds of this invention will be effective in treating generalized anxiety disorder in patients who have been diagnosed as having this disorder based upon the diagnostic criteria described in DSM-IV. It is further contemplated that the compounds of the invention will be effective in reducing symptoms of this disorder, such as the following: excessive worry and anxiety, difficulty controlling worry, restlessness or feeling keyed up or on edge, being easily fatigued, difficulty concentrating or mind going blank, irritability, muscle tension, or sleep disturbance. It is also contemplated that the compounds of this invention will be effective in preventing relapse of general anxiety disorder.

The invention provides a method of treating generalized anxiety disorder in a subject, which comprises administering to the subject an amount of any of the compounds of the invention effective to treat the subject's generalized anxiety disorder.

Post-traumatic stress disorder (PTSD), as defined by DSM-III-R/IV (American Psychiatric Association, 1987, American Psychiatric Association, 1994a), requires exposure to a traumatic event that involved actual or threatened death or serious injury, or threat to the physical integrity of self or others, and a response which involves intense fear, helplessness, or horror. Symptoms that occur as a result of exposure to the traumatic event include re-experiencing of the event in the form of intrusive thoughts, flashbacks or dreams, and intense psychological distress and physiological reactivity on exposure to cues to the event; avoidance of situations reminiscent of the traumatic event, inability to recall details of the event, and/or numbing of general responsiveness manifested as diminished interest in significant activities, estrangement from others, restricted range of affect, or sense of foreshortened future; and symptoms of autonomic arousal including hypervigilance, exaggerated startle response, sleep disturbance, impaired concentration, and irritability or outbursts of anger. A PTSD diagnosis requires that the symptoms are present for at least a month and that they cause clinically significant distress or impairment in social, occupational, or other important areas of functioning.

It is contemplated that the compounds of this invention will be effective in treating PTSD in patients who have been diagnosed as having PTSD based upon the administration of any of the following tests: Clinician-Administered PTSD Scale Part 2 (CAPS), the patient-rated Impact of Event Scale (IES). It is further contemplated that the compounds of the invention will be effective in inducing improvements in the scores of the CAPS, IES, CGI-Severity of Illness or CGI-Global Improvement tests. It is also contemplated that the compounds of this invention will be effective in preventing relapse of PTSD.

The invention provides a method of treating post-traumatic stress disorder in a subject, which comprises administering to the subject an amount of any of the compounds of the invention effective to treat the subject's post-traumatic stress disorder.

The invention also provides a method of treating a subject suffering from dysthymic disorder, bipolar I or II disorder, schizoaffective disorder, a cognitive disorder with depressed mood, a personality disorder, insomnia, hypersomnia, narcolepsy, circadian rhythm sleep disorder, nightmare disorder, sleep terror disorder or sleepwalking disorder.

The invention provides a method of alleviating the symptoms of a disorder in a subject, which comprises administering to the subject an amount of a GalR3 antagonist effective to alleviate the symptoms, wherein the GalR3 antagonist is any of the compounds of the invention. In one embodiment, the disorder is depression. In one embodiment, the disorder is anxiety. In one embodiment, the disorder is major depressive disorder. In one embodiment, the disorder is obsessive compulsive disorder. In one embodiment, the disorder is panic disorder, with or without agoraphobia. In one embodiment, the disorder is social anxiety disorder. In one embodiment, the disorder is generalized anxiety disorder. In one embodiment, the disorder is post-traumatic stress disorder.

The invention provides a method of treating a subject suffering from a disorder mediated by the GalR3 receptor comprising administering to a subject in need of such treatment a therapeutically effective amount of any of the compounds of the invention. In one embodiment, the disorder is depression. In one embodiment, the disorder is anxiety. In one embodiment, the disorder is major depressive disorder. In one embodiment, the disorder is obsessive compulsive disorder. In one embodiment, the disorder is panic disorder, with or without agoraphobia. In one embodiment, the disorder is social anxiety disorder. In one embodiment, the disorder is generalized anxiety disorder. In one embodiment, the disorder is post-traumatic stress disorder.

This invention provides a method of treating a subject suffering from an abnormality, wherein the abnormality is alleviated by decreasing the activity of a GalR3 receptor which comprises administering to the subject an amount of a compound of the invention which is a GalR3 antagonist effective to treat the subject's abnormality.

In separate embodiments, the abnormality is depression, anxiety, major depressive disorder, obsessive compulsive disorder, panic disorder with or without agoraphobia, social anxiety disorder, generalized anxiety disorder or post-traumatic stress disorder.

In the present invention a "therapeutically effective amount" is an amount of a compound which, when administered to a subject suffering from a disease causes a reduction, remission, or regression of the disease and/or of symptoms associated with that disease. In this invention, a "subject" includes any vertebrate, more particularly any mammal, e.g. any human or canine.

In one embodiment, the amount of the compound is from about 0.01 to about 1000 mg per day. In another embodiment, the amount of the compound is from about 0.1 to about 500 mg per day. In another embodiment, the amount of the compound is from about 1.0 to about 200 mg per day. In yet another embodiment, the amount of the compound is from about 10 to about 100 mg per day.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

Throughout the invention, the term "binding affinity" describes the concentration of a compound required to occupy one-half of the binding sites in a receptor population, as detectable by radioligand binding. Binding affinity concentration can be represented as $K_i$, inhibition constant, or $K_D$, dissociation constant.

The term "selectivity of binding affinity" refers to the ability of a chemical compound to discriminate one receptor from another. For example, a compound showing selectivity for receptor A versus receptor B will bind receptor A at lower concentrations than those required to bind receptor B.

The term "antagonist" refers to a compound which binds to, and decreases the activity of, a receptor in the presence of an agonist. In the case of a G-protein coupled receptor, activation may be measured using an appropriate second messenger system which is coupled to the receptor in a cell or tissue in which the receptor is expressed. Some specific but by no means limiting examples of well-known second messenger systems are adenylate cyclase, intracellular calcium mobilization, ion channel activation, guanylate cyclase, inositol phospholipid hydrolysis, and MAP kinase activation. Conversely, the term "agonist" refers to a compound which binds to, and increases the activity of, a receptor as compared with the activity of the receptor in the absence of any agonist. Methods to perform second messenger assays are described in PCT International Publication No. 97/46250 and in PCT International Publication No. 98/15570, the contents of which are hereby incorporated by reference.

In the case that a receptor has activity in the absence of an agonist (constitutive receptor activity) the antagonist may act as an inverse agonist or an allosteric modulator, as opposed to a neutral antagonist, and suppress receptor signaling independent of the agonist (Lutz and Kenakin, 1999). The categories of "antagonist compounds" are therefore seen to include 1) neutral antagonists (which block agonist actions but do not affect constitutive activity); 2) inverse agonists (which block agonist actions as well as constitutive activity by stabilizing an inactive receptor conformation); 3) and allosteric modulators (which block agonist actions to a limited extent and which may also block constitutive activity through allosteric regulation). The probability that an antagonist is neutral and therefore of "zero efficacy" is relatively low, given that this would require identical affinities for different tertiary conformations of the receptor. Thus, Kenakin proposed in 1996 that, "with the development of sensitive test systems for the detection of inverse agonism will come a reclassification of many drugs. It might be observed that numerous previously classified neutral antagonists may be inverse agonists" (Kenakin, 1996). Indeed, there is now evidence from studies with known pharmacological agents to support the existence of inverse agonists for numerous receptors, including histamine, $5HT_{1A}$, $5HT_{2C}$, cannabinoid, dopamine, calcitonin and human formyl peptide receptors, among others (de Ligt, et al, 2000; Herrick-Davis, et al, 2000; Bakker, et al, 2000). In the case of the $5HT_{2C}$ receptor, clinically effective atypical antipsychotics drugs such as sertindole, clozapine, olanzapine, ziprasidone, risperidone, zotepine, tiospirone, fluperlapine and tenilapine displayed potent inverse activity whereas typical antipsychotic drugs such as chlorpromazine, thioridazine, spiperone and thiothixene were classified as neutral antagonists (Herrick-Davis et al, 2000). In the case of the histamine $H_1$ receptor, the therapeutically used anti-allergics cetirizine, loratadine and epinastine were found to be inverse agonists. These findings further extend the idea that many compounds previously thought of as neutral antagonists will be reclassified as inverse agonists when tested in a constitutively active receptor system (de Ligt et al, 2000).

For the purpose of the claimed invention, a GalR3 antagonist useful in the treatment of depression is one which a) selectively binds to the GalR3 receptor, and b) displays antidepressant activity in the rat Forced Swim Test. Furthermore, a GalR3 antagonist useful in the treatment of anxiety is one which a) selectively binds to the GalR3 receptor, and b) displays anxiolytic activity in the rat Social Interaction. Also for the purpose in the present invention, a GalR3 antagonist useful in the treatment of depression and anxiety, is one which a) selectively binds to the GalR3 receptor, b) displays antidepressant activity in the rat Forced Swim Test, and c) displays anxiolytic activity in the rat Social Interaction Test.

In order to test compounds for selective binding to the human GalR3 receptor the cloned cDNAs encoding both the human and rat GALR1 and GALR2 receptors may be used. The cloning and assay methods for the human and rat GALR1 receptors may be found in PCT International Publication No. WO 95/22608, the contents of which are hereby incorporated by reference. The cloning and assay methods for the human and rat GALR2 receptors may be found in PCT International Publication No. WO 97/26853, the contents of which are hereby incorporated by reference.

The present invention provides for a method of determining the binding affinity of a GalR3 antagonist, wherein the GalR3 antagonist is dissolved in a "suitable solvent". A "suitable solvent" means one which permits the measurement of binding affinity of the GalR3 antagonist to the human GalR3 receptor at concentrations less than 1 $\mu$M, preferably less than 100 nM. Examples of solvents include, but are not limited to, DMSO, ethanol, N,N-dimethylacetamide, or water. The preferred solvent is the solvent which permits the measurement of binding affinity of a GalR3 antagonist at the lowest concentration.

This invention will be better understood from the Experimental Details which follow hereafter. However, one skilled in the art will readily appreciate hereafter that the specific methods and results discussed are merely illustrative of the invention as described more fully in the claims which follow thereafter.

Experimental Section

I. Synthesis of Chemical Compounds

General Methods: All reactions were performed under an Argon atmosphere and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.) Anhydrous solvents were purchased from Aldrich Chemical Company (Milwaukee, Wis.) and used as received. The examples described in the patent were named using ACD/Name program (version 2.51, Advanced Chemistry Development Inc., Toronto, Ontario, M5H2L3, Canada). Unless otherwise noted, the $^1$H spectra were recorded at 400 MHz (Bruker, Model: Avance) with tetramethylsilane as internal standard. s=singlet; d=doublet; t=triplet; q=quartet; p=quintet; sextet; septet; br=broad; m=multiplet. Elemental analyses were performed by Robertson Microlit Laboratories, Inc. Unless otherwise noted, mass spectra were obtained on a VG Patform II instrument using electrospray (ESI-MS) and MH$^+$ is reported. Thin-layer chromatography (TLC) was carried out on glass plates precoated with silica gel 60 F$_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh). Melting points (mp) were determined in open capillary tubes on a Mel-Temp apparatus and are uncorrected.

Scheme 1.
Synthesis of Substituted 2,4,6-Triamino-pyrimidines.

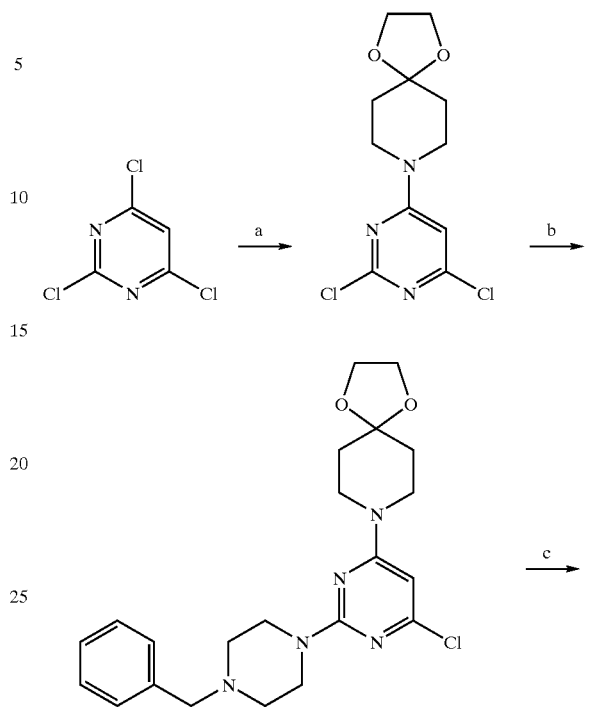

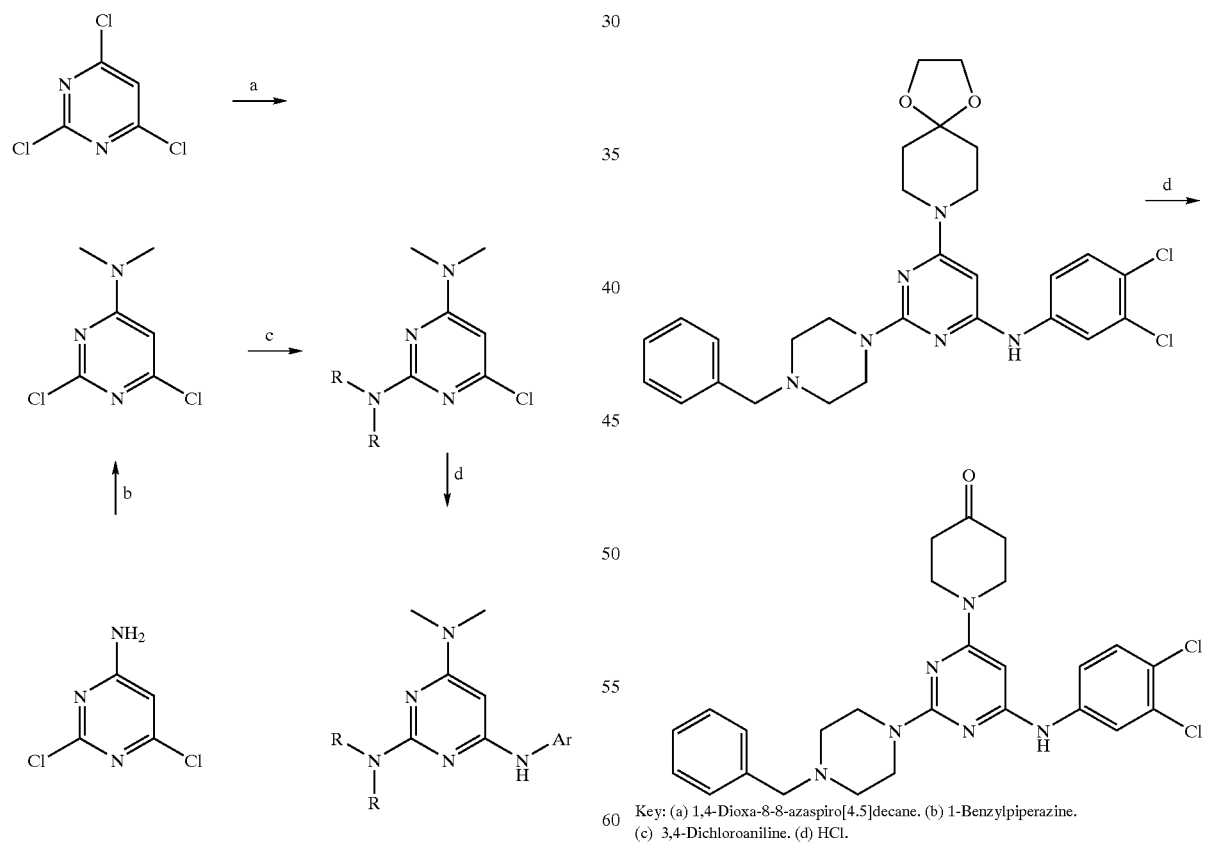

Key: (a) Dimethylamine. (b) CH$_3$I, NaH. (c) RRNH where RRNH is a primary or secondary amine. (d)Ar—NH$_2$, Pd(0) catalyst where Ar is aryl.

Scheme 2. Synthesis of the Compound of Example 53.

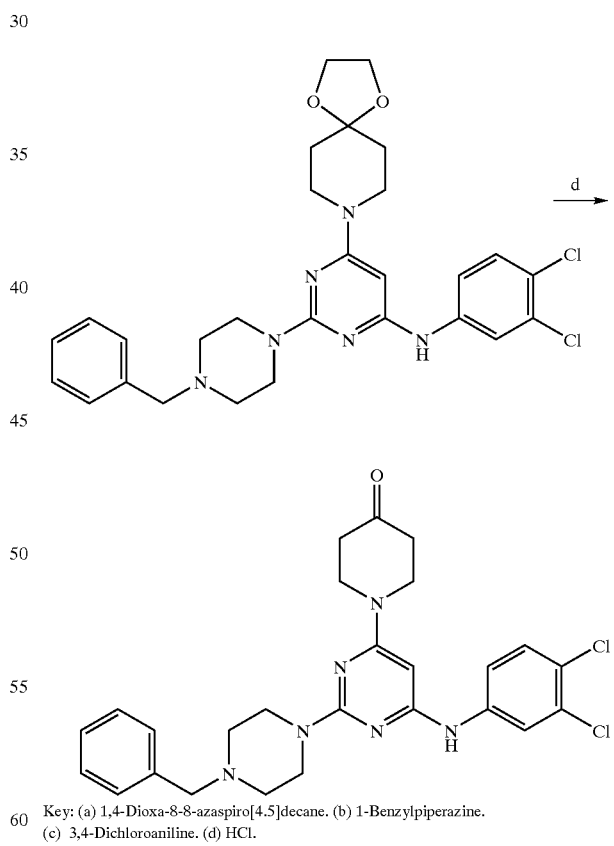

Key: (a) 1,4-Dioxa-8-8-azaspiro[4.5]decane. (b) 1-Benzylpiperazine. (c) 3,4-Dichloroaniline. (d) HCl.

Key: (a) Dimethylamine. (b) CH$_3$I, NaH. (c) RRNH where RRNH is a primary or secondary amine. (d) Ar—NH$_2$, Pd (0) catalyst where Ar is aryl.

Scheme 3. Alternate Synthesis of Substituted 2,4,6,-Triaminopyrimidines.

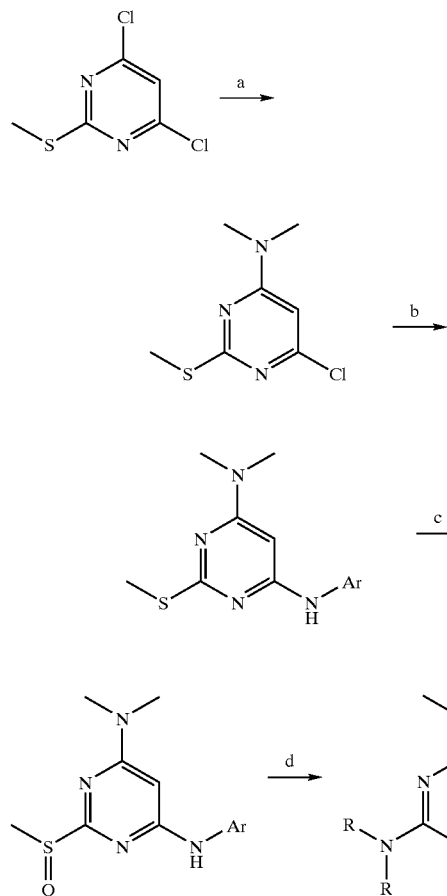

Key: (a) Dimethylamine. (b) NaH, Ar—NH2, THF where Ar is aryl.
(c) m-CPBA. (d) RRNH where RRNH is a primary or secondary amine.

Scheme 4. Synthesis of the Compound of Example 46.

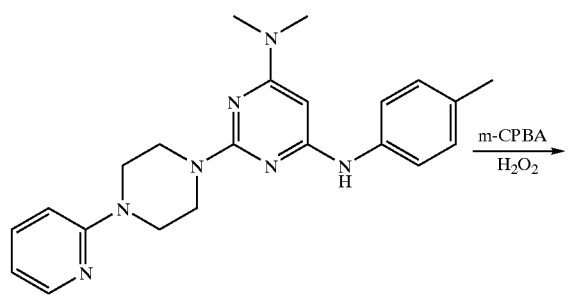

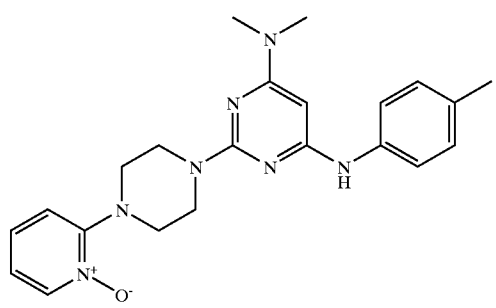

Scheme 5. Synthesis of the Compound of Example 43.

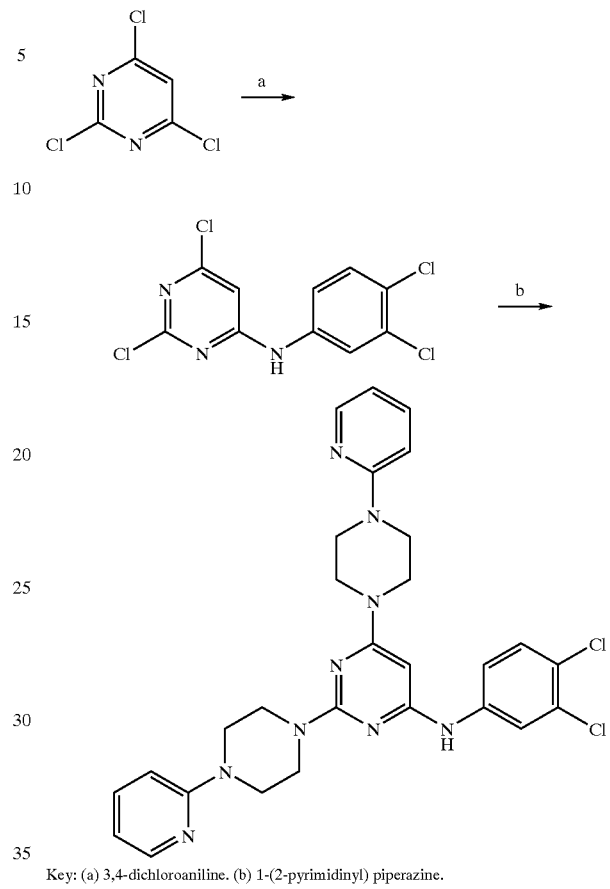

Key: (a) 3,4-dichloroaniline. (b) 1-(2-pyrimidinyl) piperazine.

Scheme 6. Synthesis of Substituted 2-Aminoanilines.

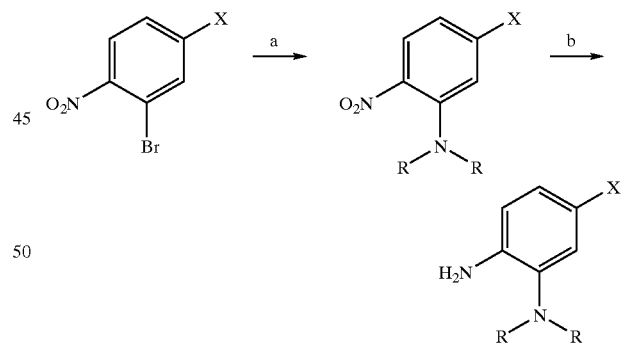

Key: (a) RRNH where RRNH is a primary or secondary amine.
(b) SnCl2.

Scheme 7. Synthesis of the Compounds of Example 33 and 40.

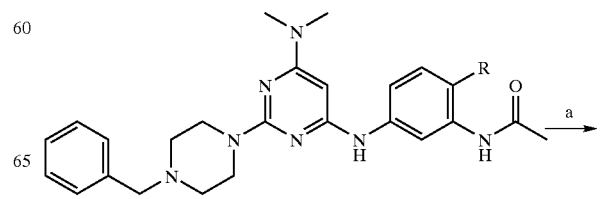

-continued

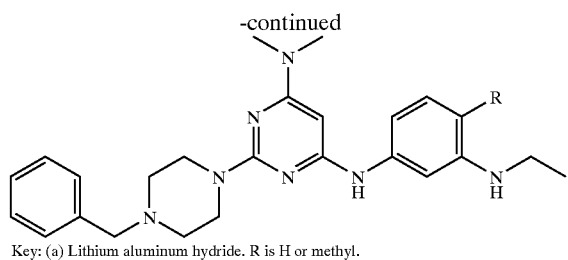

Key: (a) Lithium aluminum hydride. R is H or methyl.

Scheme 8. Synthesis of the Compounds of Examples 26, 49 and 50.

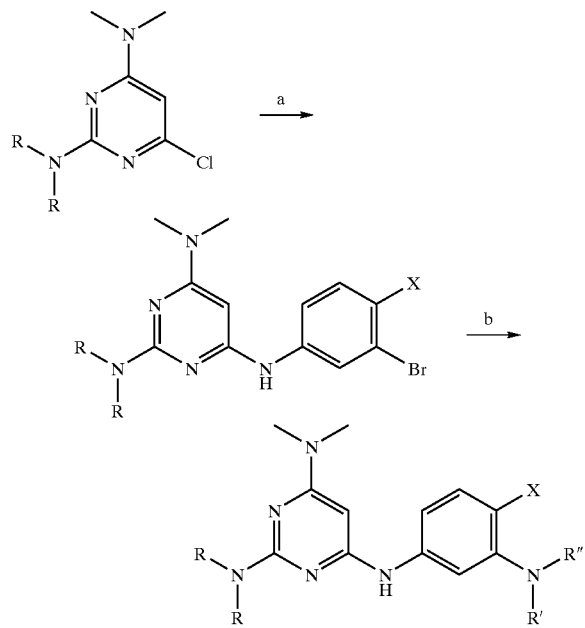

Key: (a) 3-Bromoaniline or 3-bromo-4-methylaniline.
(b) Primary or secondary amine, Pd(0) catalyst.
RRN is 1-[4-(pyridinyl) piperazinyl] or cis-3,5-dimethyl
morpholin-1-yl. R' is H or methyl. R" is isopropyl,
benzyl or sec-butyl.

Synthetic Procedures
Procedure A, Step 1

2,6-DICHLORO-N,N-DIMETHYL-4-PYRIMIDINAMINE: Sodium hydride (0.13 g, 0.79 mmol) was added to a solution of 2,6-dichloro-4-pyrimidinamine (0.40 g, 0.95 mmol) in dry tetrahydrofuran (5 mL) and stirred for 10 minutes. Methyl iodide (0.060 mL, 0.95 mmol) was added and the resulting solution was stirred for 3 hours at room temperature. The solution was quenched with aqueous ammonium chloride/ammonium carbonate, extracted with EtOAc and the extracts were dried over anhydrous sodium sulfate. The solvent was removed and the resulting crude product was purified by flash chromatography [eluent: hexane/EtOAc (2:1)], giving the desired product (70 mg, 0.36 mmol, 46%).

Procedure A, Step 1 (Alternate Procedure)
2,6-DICHLORO-N,N-DIMETHYL-4-PYRIMIDINAMINE: Dimethylamine hydrochloride (35.6 g, 0.44 mol) was added to a vigorous stirring solution of 2,4,6-trichloropyrimidine (80.0g, 0.44 mol) in $CH_2Cl_2$ (1.5 L) at −78° C. Triethylehtylmine (88.2 g, 0.87 mol) was added dropwise to the above mixture and stirred for 3 hours at −78° C. The resulting mixture was brought to 0° C. over a period of 3 hours and the reaction was then quenched with water (250 mL). The organic layer was separated, washed with aqueous citric acid (2×100 mL), brine (2×200 mL), dried over $Na_2SO_4$ and concentrated in vacuo. The crude product was purified by column chromatography [eluent: EtOAc/hexanes (1:9)], giving the desired product (59.9 g, 60%).

Procedure A, Step 2
N-{6-CHLORO-2-[4-(2-PYRIDINYL)-1-PIPERAZINYL]-4-PYRIMIDINYL}-N,N-DIMETHYLAMINE: A mixture of N,N-diisopropylethylamine (4.6 g. 0.036 mol), 4-N,N-dimethylamino-2,6-dichloropyrimidine (4.8 g, 0.025 mol) and 1-(2-pyridinyl)piperazine (4.6 g, 0.028 mol) in toluene (100 mL) was heated at reflux for 16 hours and then cooled to room temperature. The crude product was treated with saturated $NaHCO_3$ (2×100 mL) and extracted with $CH_2Cl_2$ (3×100 mL). The organic layer was washed with brine (2×100 mL), dried over $Na_2SO_4$, concentrated in vacuo, and purified by chromatography [eluent: hexane/EtOAc (1:4)], giving the desired product (5.45 g, 65%). ESI-MS m/z: 319 (MH$^+$).

Procedure A, Step 3
$N^4$-[2-(ISOPROPYLAMINO)-4-METHYLPHENYL]-$N^6$,$N^6$-DIMETHYL-2-[4-(2-PYRIDINYL)-1-PIPERAZINYL]-4,6-PYRIMIDINEDIAMINE: Sodium tert-butoxide (100 mg, 1.04 mmol) was added to a solution of $N^2$-isopropyl-4-methyl-1,2-benzenediamine (100 mg 0.60 mmol) and N-{6-chloro-2-[4-(2-pyridinyl)-1-piperazinyl]-4-pyrimidinyl}-N,N-dimethylamine (100 mg, 0.30 mmol) in 1,4-dioxane (10 mL). Tris (dibenzylidineacetone)dipalladium (8 mg, 0.008 mmol) and 2,2'-Bis(diphenylphosphino)-1,1'binapthyl (10 mg, 0.016 mmol) were added to this mixture and heated at 110° C. for 10 hours. The resulting mixture was cooled to room temperature, concentrated in vacuo, and purified by preparative thin-layer chromatography [eluent: hexane/EtOAc (1:1)], giving the desired product (30 mg, 23%).

Procedure B, Step 1
8-(2,6-DICHLORO-4-PYRIMIDINYL)-1,4-DIOXA-8-AZASPIRO[4.5]DECANE: 1,4-dioxa-8-azaspiro[4.5] decane (19.52 g, 136.3 mmol) was added to a solution of 2,4,6-trichloropyrimidine (25.0 g, 136 mmol) in $CH_2Cl_2$ (475 mL) at −78° C. with vigorous stirring. Diisopropylethylamine (26.4 g, 205 mmol) was added dropwise to the above mixture and stirred for 3 hours at −78° C. The resulting mixture was brought to 0° C. over a period of 3 hours and quenched with water (250 mL). The organic layer was separated, washed with aqueous citric acid (2×100 mL), brine (2×200 mL), dried over anhydrous $Na_2SO_4$ and concentrated in vacuo. The crude product was purified by column chromatography [eluent: EtOAc/hexanes (1:9)], giving the desired product (7.40 g, 19%).

Procedure B, Step 2
8-[2-(4-BENZYL-1-PIPERAZINYL)-6-CHLORO-4-PYRIMIDINYL]-1,4-DIOXA-8-AZASPIRO[4.5] DECANE: 1-Benzylpiperazine (7.59 g, 43.1 mmol) was added to a solution of 8-(2,6-dichloro-4-pyrimidinyl)-1,4-dioxa-8-azaspiro[4.5]decane (10.0 g, 34.5 mmol) in tetrahydrofuran (100 mL), followed by diisopropylamine (9.26 g, 71.7 mmol). The reaction mixture was then heated at reflux overnight. The crude product was concentrated under reduced pressure and the residue was re-dissolved in $CH_2Cl_2$ and then washed with aqueous citric acid (2×100 mL) and brine (2×200 mL). The organic layer was dried over -anhydrous $Na_2SO_4$ and filtered. Upon standing, crystallization occurred, giving the desired product (12.4 g, 84%).

Procedure B, Step 3

2-(4-BENZYL-1-PIPERAZINYL)-N-(3,4-DICHLOROPHENYL)-6-(1,4-DIOXA-8-AZASPIRO[4.5]DEC-8-YL)-4-PYRIMIDINAMINE: A mixture of 3,4-dichloroaniline (1.7 g, 10.5 mmol) and NaH (0.50 g, 20.9 mmol) in tetrahydrofuran (20 mL) was heated at reflux for 30 minutes and then cooled to room temperature. A solution of 8-[2-(4-benzyl-1-piperazinyl)-6-chloro-4-pyrimidinyl]-1,4-dioxa-8-azaspiro[4.5]decane (3.0 g, 7.0 mmol) in tetrahydrofuran (30 mL) was added to this mixture and the resulting solution was stirred for 22.5 hours. The reaction mixture was quenched with saturated NH$_4$Cl, concentrated under reduced pressure, and redissolved in EtOAc. The organic layer was separated and washed with aqueous citric acid (2×300 mL), water (2×300 mL), and brine (2×300 mL). The crude product was purified by column chromatography [eluent: EtOAc/hexane (1:4)], giving the desired product (1.7 g, 44%).

Procedure B, Step 4

1-[2-(4-BENZYL-1-PIPERAZINYL)-6-(3,4-DICHLOROANILINO)-4-PYRIMIDINYL]-4-PIPERIDINONE: A mixture of 2-(4-benzyl-1-piperazinyl)-N-(3,4-dichlorophenyl)-6-(1,4-dioxa-8-azaspiro[4.5]dec-8-yl)-4-pyrimidinamine (100 mg, 0.18 mmol) and 4M HCl (10 mL) in dioxane (20 mL) was stirred at room temperature for 24 hours. The crude product was purified by preparative thin-layer chromatography [eluent: EtOAc/hexane (2:3) with 1% NH$_3$ in methanol], giving the desired product (10 mg, 11%).

Procedure C, Step 1

N-[6-CHLORO-2-(METHYLSULFANYL)-4-PYRIMIDINYL]-N,N-DIMETHYLAMINE: A mixture of 4,6-dichloro-2-(methylsulfanyl)pyrimidine (5.0 g, 26 mmol), N,N-diisopropylethylamine (3.1 g, 26 mmol), triethylamine (7.15 mL, 51 mmol), and N,N-dimethylamine hydrochloride (2.09 g, 26 mmol) in tetrahydrofuran (50 mL) was heated at reflux for 16 hours. The solvent was removed and the crude material was redissolved in EtOAc and washed with a solution of citric acid (2×100 mL), followed by water (2×100 mL) and brine (2×100 mL). The organic layers were combined, dried over anhydrous MgSO$_4$, concentrated and purified by flash chromatography [eluent: EtOAc/hexane (1:19)], giving the desired product (3.89 g, 73%).

Procedure C, Step 2

N$^4$-[3-(BENZYLOXY) PHENYL]-N$^6$,N$^6$-DIMETHYL-2-(METHYLSULFANYL)-4,6-PYRIMIDINEDIAMINE: A mixture of 3-(benzyloxy)aniline (5.13 g) and NaH (1.37 g) in tetrahydrofuran (15 mL) was refluxed for 30 minutes and then cooled to room temperature. A solution of N-[6-chloro-2-(methylsulfanyl)-4-pyrimidinyl]-N,N-dimethylamine (3.5 g) in tetrahydrofuran (35 mL) was added to this mixture and the resulting solution was stirred for 22.5 hours. The reaction mixture was quenched with saturated NH$_4$Cl. Then the crude product was concentrated under reduced pressure and redissolved in EtOAc. The organic layer was separated and washed with aqueous citric acid (2×300 mL), water (2×300 mL) and brine (2×300 mL). The crude product was purified by column chromatography [eluent: EtOAc/hexane (1:4)], giving the desired product (5.9 g, 94%).

Procedure C, Step 3

N$^4$-[3-(BENZYLOXY)PHENYL]-N$^6$,N$^6$-DIMETHYL-2-[4-(2-PYRIMIDINYL)-1-PIPERAZINYL]-4,6-PYRIMIDINEDIAMINE: A solution of N$^4$-[3-(benzyloxy)phenyl]-N$^6$,N$^6$-dimethyl-2-(methylsulfanyl)-4,6-pyrimidinediamine (5.5 g, 15 mmol) and m-chloroperbenzoic acid (5.19 g) in CH$_2$Cl$_2$ at 0° C. was stirred for 1 hour. The reaction mixture was slowly brought to room temperature and quenched with a solution of sodium sulfite. The organic layer was separated and washed with NaHCO$_3$ solution (3×250 mL), dried over anhydrous MgSO$_4$, concentrated, and purified by column chromatography [eluent: chloroform/methanol (94:6)], giving N$^4$-[3-(benzyloxy)phenyl]-N$^6$,N$^6$-dimethyl-2-(methylsulfinyl)-4,6-pyrimidinediamine (3.98, 69%).

A mixture of N$^4$-[3-(benzyloxy)phenyl]-N$^6$,N$^6$-dimethyl-2-(methylsulfinyl)-4,6-pyrimidinediamine (30 mg, 0.078 mmol) and 2-(1-piperazinyl)pyrimidine dihydrochloride (74 mg, 0.312 mmol) in chlorobenzene (2 mL) was heated at reflux for 15 hours. The crude product was purified by preparative thin-layer chromatography [eluent: hexane/EtOAc (7:3)], giving the desired product (16 mg, 42%).

Procedure D

N$^4$,N$^4$-DIMETHYL-N$^6$-(4-METHYLPHENYL)-2-{4-[1-OXIDO-3-(TRIFLUOROMETHYL)-2-PYRIDINYL]-1-PIPERAZINYL}-4,6-PYRIMIDINEDIAMINE: A mixture of N$^4$,N$^4$-dimethyl-N$^6$-(4-methylphenyl)-2-{4-[3-(trifluoromethyl)-2-pyridinyl]-1-piperazinyl}-4,6-pyrimidinediamine (150, mg, 0.33 mmol), m-chloroperbenzoic acid (56 mg, 0.33 mmol) and 30% H$_2$O$_2$ (2 drops) were stirred at 0° C. for 24 hours. The crude product was then treated with saturated NaHCO$_3$ solution (2×100 mL). The organic layer was separated, dried over MgSO$_4$, concentrated in vacuo. The residue was purified by preparative thin-layer chromatography (eluent: EtOAc), giving the desired product (12 mg, 8%).

Procedure E, Step 1

2,6-DICHLORO-N-(3,4-DICHLOROPHENYL)-4-PYRIMIDINAMINE: A solution of 3,4-dichloroaniline (8.87 g, 54.8 mmol) in ethanol (40 mL) was added to a solution of 2,4,6-trichloropyrimidine (10.0 g, 54.8 mmol) in ethanol (20 mL) followed by aqueous Na$_2$CO$_3$ (4.61 g, 43.5 mmol) at 0° C. The reaction mixture was stirred at room temperature overnight. The crude mixture was diluted with water (100 mL), and the resulting precipitate was filtered and dried (10.2 g, 61%). ESI-MS m/z: 307 (MH$^+$).

Procedure E, Step 2

6-CHLORO-N-(3,4-DICHLOROPHENYL)-2-[4-(2-PYRIDINYL)-1-PIPERAZINYL]-4-PYRIMIDINAMINE and N-(3,4-DICHLOROPHENYL)-2,6-BIS[4-(2-PYRIDINYL)-1-PIPERAZINYL]-4-PYRIMIDINAMINE: A mixture of 2,6-dichloro-N-(3,4-dichlorophenyl)-4-pyrimidinamine (2.74 g, 8.94 mmol), 1-(2-pyridinyl)piperazine (2.18 g, 13.41 mmol), triethylamine (1.81 g, 17.9 mmol), and diisopropylethylamine (4.74 g, 36.7 mmol) in tetrahydrofuran (20 mL) was heated at reflux for 48 hours. The crude product was concentrated under reduced pressure and redissolved in CH$_2$Cl$_2$ and washed with water (2×100 mL) and brine (2×100 mL). The crude product was purified by column chromatography [eluent: EtOAc/hexanes (1:4)], giving 6-chloro-N-(3,4-dichlorophenyl)-2-[4-(2-pyridinyl)-1-piperazinyl]-4-pyrimidinamine (1.07 g, 27%). ESI-MS m/z: 436 (MH$^+$). N-(3,4-Dichlorophenyl)-2,6-bis[4-(2-pyridinyl)-1-piperazinyl]-4-pyrimidinamine was also isolated as a by-product (0.93 g, 19%). ESI-MS m/z: 563 (MH$^+$).

Procedure F, Step 1

N-ISOPROPYL-5-METHYL-2-NITROANILINE: A mixture of 2-fluoro-4-methyl-1-nitrobenzene (250 mg, 1.6 mmol), triethylamine (200 mg, 2.0 mmol), and 2-propanamine (200 mg, 3.4 mmol) in tetrahydrofuran (1 mL) was heated at 25° C. for 5 hours. The crude product was purified by preparative thin-layer chromatography [eluent: hexane/EtOAc (1:2)], giving the desired product (150 mg, 48%).

Procedure F, Step 2

N$^2$-ISOPROPYL-4-METHYL-1,2-BENZENEDIAMINE: A mixture of N-isopropyl-5-methyl-2-nitroaniline (150 mg, 0.77 mmol), SnCl$_2$ (0.5 g, 2.6 mmol), 0.5M HCl (10 mL), and water (20 mL) was stirred at room temperature for 16 hours. The crude product was partitioned in a mixture of aqueous NaHCO$_3$ and CH$_2$Cl$_2$. The organic layer was separated and concentrated to obtain the desired product (120 mg, 95%).

Procedure G 2-(4-BENZYL-1-PIPERAZINYL)-N$^4$-[3-(ETHYLAMINO)-4-METHYLPHENYL]-N$^6$,N$^6$-DIMETHYL-4,6-PYRIMIDINEDIAMINE: A mixture of N-(5-{[2-(4-benzyl-1-piperazinyl)-6-(dimethylamino)-4-pyrimidinyl]amino}-2-methylphenyl)acetamide (40 mg, 0.08 mmol) and lithium aluminum hydride (76 mg, 2 mmol) in tetrahydrofuran (3 mL) was heated at 90° C. for 12 hours. The crude product was filtered through Celite® and purified by preparative thin-layer chromatography [eluent: EtOAc/hexane (1:1)], giving the desired product (27 mg, 76%).

Procedure H

N$^4$-[3-(ISOPROPYLAMINO)-4-METHYLPHENYL]-N$^6$,N$^6$-DIMETHYL-2-[4-(2-PYRIDINYL)-1-PIPERAZINYL]-4,6-PYRIMIDINEDIAMINE: Potassium tert-butoxide (112 mg, 1.00 mmol) was added to a solution of 2-propanamine (287 mg, 5.0 mmol) and 2-(4-benzyl-1-piperazinyl)-N$^4$-(3-bromo-4-methylphenyl)-N$^6$,N$^6$-dimethyl-4,6-pyrimidinediamine (65 mg, 0.14 mmol) in toluene (10 mL). Tris(dibenzylidineacetone)dipalladium (4 mg, 0.004 mmol) and 2,2'-bis(diphenylphosphino)-1,1'-binapthyl (6 mg, 0.01 mmol) were added and the resulting mixture was heated at 85° C. for 16 hours. The mixture was then cooled to room temperature, concentrated in vacuo and purified by preparative TLC [eluent: EtOAc/hexane (1:3)], giving the desired product (20 mg, 32%).

Procedure H (Alternate Procedure)

N$^4$-{3-[BENZYL(METHYL)AMINO]-4-METHYLPHENYL}-2-(CIS-2,6-DIMETHYLMORPHOLINYL)-N$^6$,N$^6$-DIMETHYL-4,6-PYRIMIDINEDIAMINE: Sodium tert-butoxide (60 mg, 0.63 mmol) was added to a solution of N$^4$-(3-bromo-4-methylphenyl)-2-(cis-2,6-dimethylmorpholinyl)-N$^6$,N$^6$-dimethyl-4,6-pyrimidinediamine (50 mg, 0.12 mmol) and N-methyl(phenyl)methanamine (50 mg, 0.40 mmol) in tetrahydrofuran (2 mL). Tris(dibenzylidineacetone) dipalladium (1 mg, 0.001 mmol) and 2,2'-bis(diphenylphosphino)-1,1'-binapthyl (2 mg, 0.003 mmol) were added to this mixture and the resulting mixture was heated at 110° C. for 16 hours. The mixture was then cooled to room temperature, concentrated in vacuo, and purified by preparative thin-layer chromatography [eluent: hexane/EtOAc (3:1)], giving the desired product (20 mg, 36%).

The compounds in Table 1 were synthesized by the methods described in Procedure B, Steps 2 and 3. Various amines were substituted for 1-benzylpiperazine in step 2 and for 3,4-dichloroaniline in step 3 as indicated in Table 1. All compounds in Table 1 were synthesized from 2,6-dichloro-N,N-dimethyl-4-pyrimidine (described in Procedure A, Step 1) which was used in place of 8-(2,6-dichloro-4-pyrimidinyl)-1,4-dioxa-8-azaspiro[4.5]decane in step 2 of Procedure B.

TABLE I

| Compound Example | Amine Used in Step 2 | Amine used in step 3 |
|---|---|---|
| 1 | 1-(3-chlorophenyl)-piperazine | p-toluidine |
| 2 | 1-(3-chlorophenyl)-piperazine | 2,3-dihydro-1H-inden-5-ylamine |
| 3 | 1-(2-chlorophenyl)-piperazine | p-toluidine |
| 4 | 1-(2-chlorophenyl)-piperazine | 2,3-dihydro-1H-inden-5-ylamine |
| 5 | 1-(2-fluorophenyl)-piperazine | p-toluidine |
| 6 | 1-(4-chlorophenyl)-piperazine | 2,3-dihydro-1H-inden-5-ylamine |
| 7 | 1-(4-chlorophenyl)-piperazine | p-toluidine |
| 8 | 1-(3-chlorophenyl)-piperazine | 3-methoxyaniline |
| 9 | 1-(3-chlorophenyl)-piperazine | 4-cyclohexylaniline |
| 10 | 1-(4-chlorophenyl)-piperazine | 4-cyclohexylaniline |
| 11 | 1-(2-chlorophenyl)-piperazine | 3-methoxyaniline |
| 12 | 1-(2-fluorophenyl)-piperazine | 2,3-dihydro-1H-inden-5-ylamine |
| 13 | 1-(2-fluorophenyl)-piperazine | 3-methoxyaniline |
| 14 | 1-(2-fluorophenyl)-piperazine | 3-chloro-4-[(trifluoromethyl)sulfanyl]aniline |
| 15 | 1-(4-chlorophenyl)-piperazine | 3-methoxyaniline |
| 16 | 1-(3-chlorophenyl)-piperazine | 3,4-dichloroaniline |
| 17 | 1-(2-chlorophenyl)-piperazine | 3,4-dimethylaniline |
| 18 | 1-(2-fluorophenyl)-piperazine | 4-cyclohexylaniline |
| 19 | 1-(2-fluorophenyl)-piperazine | 3,4-dimethylaniline |
| 20 | 1-(3-chlorophenyl)-piperazine | 3-chloro-4-[(trifluoromethyl)sulfanyl]aniline |
| 21 | 1-(2-chlorophenyl)-piperazine | 3,4-dichloroaniline |
| 22 | 1-(2-chlorophenyl)-piperazine | 3-chloro-4-[(trifluoromethyl)sulfanyl]aniline |
| 23 | 1-(4-chlorophenyl)-piperazine | 3,4-dimethylaniline |
| 24 | 1-(2-fluorophenyl)-piperazine | 3-(benzyloxy)aniline |
| 25 | 1-(2-chlorophenyl)-piperazine | 3-(benzyloxy)aniline |
| 27 | 1-(3-chlorophenyl)-piperazine | 3-(benzyloxy)aniline |
| 29 | 1-(2-fluorophenyl)-piperazine | 3,4-dichloroaniline |
| 30 | 1-(4-chlorophenyl)-piperazine | 3-chloro-4-[(trifluoromethyl)sulfanyl]aniline |
| 31 | 1-(4-chlorophenyl)-piperazine | 3-(benzyloxy)aniline |
| 32 | 1-(3-chlorophenyl)-piperazine | 3,4-dimethylaniline |
| 34 | cis-2,6-dimethyl-morpholine | 3-(benzyloxy)aniline |
| 35 | N-methyl (tetrahydro-2-furanyl)methanamine | 3-(benzyloxy)aniline |
| 36 | piperidine | 3-(benzyloxy)aniline |
| 37 | pyrrolidine | 3-(benzyloxy)aniline |
| 38 | 3,5-dimethylpiperidine | 3-(benzyloxy)aniline |
| 39 | benzylamine | p-toluidine |
| 42 | Indoline | 3-(benzyloxy)aniline |
| 48 | 2,6-dimethylmorpholine | 3-(benzyloxy)aniline |
| 51 | (cis-2,6-dimethyl-morpholine | 3,4-dichloroaniline |
| 54 | 1-(4-chlorophenyl)-piperazine | 3,4-dichloroaniline |

The compound of Example 26 was synthesized by the methods described in Procedures A and H.

The compound of Example 28 was synthesized by the methods described in Procedure A, except that $N^1,N^1$-dimethyl-1,3-benzenediamine was used in place of $N^3$-isopropyl-4-methyl-1,3-benzenediamine in step 3.

The compound of Example 33 was synthesized by the methods described in Procedure A, except that 1-benzylpiperazine was used in place of 1-(2-pyridinyl)piperazine in step 2 and $N^3$-ethyl-4-methyl-1,3-benzenediamine was used in place of $N^3$-isopropyl-4-methyl-1,3-benzenediamine in step 3.

The compound of Example 40 was synthesized by the methods described in Procedure A, except that 1-benzylpiperazine was used in place of $N^3$-isopropyl-4-methyl-1,3-benzenediamine in step 3.

The compound of Example 41 was synthesized by the methods described in Procedure C.

The compound of Example 43 was synthesized by the methods described in Procedure E.

The compound of Example 44 was synthesized by the methods described in Procedures A and F, except that diethylamine was used in place of 2-propanamine in step 1 of Procedure F and the resulting aniline after step 2 of Procedure F was used in place of $N^2$-isopropyl-4-methyl-1,2-benzenediamine in step 3 of Procedure A.

The compound of Example 45 was synthesized by the methods described in Procedures A and F.

The compound of Example 46 was synthesized by the methods described in Procedure D.

The compound of Example 47 was synthesized by the methods described in Procedure A except that 1-ethyl-1H-indol-6-amine was used in step 3.

The compound of Example 49 was synthesized by the methods described in Procedures A and H (alternate procedure), except that cis-3,5-dimethylmorpholine was used in place of 1-(2-pyridinyl)piperazine in step 2 of Procedure A.

The compound of Example 50 was synthesized by the methods described in Procedures A and H, except that cis-3,5-dimethylmorpholine was used in place of 1-(2-pyridinyl)piperazine in step 2 of Procedure A and sec-butylamine was used in place of 2-propanamine in Procedure H.

The compound of Example 52 was synthesized by the methods described in Procedure A.

The compound of Example 53 was synthesized by the methods described in Procedure B.

EXAMPLE 1

2-[4-(3-CHLOROPHENYL)-1-PIPERAZINYL]-$N^4,N^4$-DIMETHYL-$N^6$-(4-METHYLPHENYL)-4,6-PYRIMIDINEDIAMINE: $^1$H NMR (CDCl$_3$) δ 7.23–6.98 (m, 6H), 6.94–6.89 (m, 1H), 6.86–6.78 (m, 1H), 6.24 (s, 1H), 5.28 (s, 1H), 3.91 (t, 4H, J=5), 3.23 (t, 4H, J=5), 2.99 (s, 6H), 2.32 (s, 3H); ESI-MS m/z: 423 (MH$^+$).

EXAMPLE 2

2-[4-(3-CHLOROPHENYL)-1-PIPERAZINYL]-$N^4$-(2,3-DIHYDRO-1H-INDEN-5-YL)-$N^6,N^6$-DIMETHYL-4,6-PYRIMIDINEDIAMINE: $^1$H NMR (CDCl$_3$) δ 7.26–6.76 (m, 7H), 6.39 (br s, 1H), 5.29 (s, 1H), 3.89 (t, 4H, J=5.2), 3.20 (t, 4H, J=5.2), 3.00 (s, 6H), 2.92–2.71 (m, 4H), 2.11–1.95 (m, 2H); ESI-MS 449 m/z: (MH$^+$)

EXAMPLE 3

2-[4-(2-CHLOROPHENYL)-1-PIPERAZINYL]-$N^4,N^4$-DIMETHYL-$N^6$-(4-METHYLPHENYL)-4,6-PYRIMIDINEDIAMINE: $^1$H NMR (CDCl$_3$) δ 7.38 (dd, 1H, J=1.5, 7.8), 7.29–7.09 (m, 2H), 7.07 (6.95 (m, 5H), 6.29 (br s, 1H), 5.28 (s, 1H), 3.96 (t, 4H, J=5.2), 3.10 (t, 4H, J=5.2), 3.00 (s, 6H), 2.33 (s, 3H); ESI-MS m/z: 423 (MH$^+$)

EXAMPLE 4

2-[4-(2-CHLOROPHENYL)-1-PIPERAZINYL]-$N^4$-(2,3-DIHYDRO-1H-INDEN-5-YL)-$N^6,N^6$-DIMETHYL-4,6-PYRIMIDINEDIAMINE: $^1$H NMR (CDCl$_3$) δ 7.38 (dd, 2H, J=1.7, 8.5), 7.25–7.14 (m, 2H), 7.07 (t, 2H, J=8.5), 6.98 (dt, 1H, J=1.7, 7.6), 6.27 (s, 1H), 5.30 (s, 1H), 3.95 (t, 4H, J=5.1), 3.09 (t, 4H, J=5.1), 3.00 (s, 6H), 2.88 (q, 4H, J=7.6), 2.17–2.02 (m, 2H); ESI-MS m/z: 449 (MH$^+$)

EXAMPLE 5

2-[4-(2-FLUOROPHENYL)-1-PIPERAZINYL]-$N^4,N^4$-DIMETHYL-$N^6$-(4-METHYLPHENYL)-4,6-PYRIMIDINEDIAMINE: $^1$H NMR (CDCl$_3$) δ 7.22–7.11 (m, 4H), 7.10–6.90 (m, 4H), 6.23 (br s, 1H), 5.28 (s, 1H), 3.95 (t, 4H, J=5.3), 3.13 (t, 4H, J=5.4), 3.00 (s, 6H), 2.33 (s, 3H); ESI-MS m/z: 407 (MH$^+$).

EXAMPLE 6

2-[4-(4-CHLOROPHENYL)-1-PIPERAZINYL]-$N^4$-(2,3-DIHYDRO-1H-INDEN-5-YL)-$N^6,N^6$-DIMETHYL-4,6-PYRIMIDINEDIAMINE: $^1$H NMR (CDCl$_3$) δ 7.24–7.12 (m, 3H), 7.09–7.04 (m, 2H), 6.89 (d, 2H, J=7.8), 6.20 (s, 1H), 5.30 (s, 1H), 3.92 (t, 4H, J=6.1), 3.19 (t, 4H, J=6.1), 3.00 (s, 6H), 2.95–2.84 (m, 4H), 2.14–2.02 (m, 2H); ESI-MS m/z: 449 (MH$^+$).

EXAMPLE 7

2-[4-(4-CHLOROPHENYL)-1-PIPERAZINYL]-$N^4,N^4$-DIMETHYL-$N^6$-(4-METHYLPHENYL)-4,6-PYRIMIDINEDIAMINE: $^1$H NMR (CDCl$_3$) δ 7.33–7.09 (m, 6H), 6.93–6.84 (m, 2H), 6.25 (br s, 1H), 5.29 (s, 1H), 3.92 (t, 4H, J=5.0), 3.19 (t, 4H, J=5.1), 2.99 (s, 6H), 2.33 (s, 3H); ESI-MS m/z: 423 (MH$^+$).

EXAMPLE 8

2-[4-(3-CHLOROPHENYL)-1-PIPERAZINYL]-$N^4$-(3-METHOXYPHENYL)-$N^6,N^6$-DIMETHYL-4,6-PYRIMIDINEDIAMINE: $^1$H NMR (CDCl$_3$) δ 7.24–7.15 (m, 2H), 7.03–6.98 (m, 1H), 6.95–6.89 (m, 1H), 6.90–6.79 (m, 2H), 6.72–6.55 (m, 2H), 6.34 (br s, 1H), 5.37 (S, 1H), 3.92 (t, 4H, J=6.3), 3.80 (s, 3H), 3.23 (t, 4H, J=6.3), 3.01 (s, 6H); ESI-MS m/z: 439 (MH$^+$).

EXAMPLE 9

2-[4-(3-CHLOROPHENYL)-1-PIPERAZINYL]-$N^4$-(4-CYCLOHEXYLPHENYL)-$N^6,N^6$-DIMETHYL-4,6-PYRIMIDINEDIAMINE: $^1$H NMR (CDCl$_3$) δ 7.41–7.09 (m, 4H), 7.01 (t, 1H, J=7.0), 6.95–6.90 (m, 1H), 6.83 (t, 1H, J=7.0), 6.63 (d, 1H, J=7.5), 6.24 (br s, 1H), 5.32 (3, 1H), 3.92 (t, 4H, J=5.0), 3.24 (t, 4H, J=5.0), 3.01 (s, 6H), 2.55–2.34 (m, 1H), 1.96–1.66 (m, 4H), 1.52–1.11 (m, 4H), 0.95–0.77 (m, 2H); ESI-MS m/z: 491 (MH$^+$).

EXAMPLE 10

2-[4-(4-CHLOROPHENYL)-1-PIPERAZINYL]-$N^4$-(4-CYCLOHEXYLPHENYL)-$N^6,N^6$-DIMETHYL-4,6-PYRIMIDINEDIAMINE: $^1$H NMR (CDCl$_3$) δ 7.25–7.18 (m, 4H), 7.15 (d, 2H, J=8.2), 6.87 (d, 2H, J=8.2), 6.31 (br s, 1H), 5.31 (s, 1H), 3.91 (t, 4H, J=5.1), 3.18 (t, 4H, J=5.1), 3.00 (s, 6H), 2.52–2.42 (m, 1H), 1.92–1.78 (m, 4H), 1.74 (d, 1H, J=11.5), 1.48–1.32 (m, 5H); ESI-MS m/z: 491 (MH$^+$).

EXAMPLE 11

2-[4-(2-CHLOROPHENYL)-1-PIPERAZINYL]-N$^4$-(3-METHOXYPHENYL)-N$^6$,N$^6$-DIMETHYL-4,6-PYRIMIDINEDIAMINE: $^1$H NMR (CDCl$_3$) δ 7.42–7.34 (m, 2H), 7.29–7.16 (m, 2H), 7.11–6.92 (m, 2H), 6.88–6.82 (m 1H), 6.62–6.53 (m, 1H), 6.37 (s, 1H), 5.31 (s, 1H), 3.96 (t, 4H, J=5.2), 3.78 (s, 3H), 3.10 (t, 4H, J=5.2), 3.00 (s, 6H); ESI-MS m/z: 439(MH$^+$).

EXAMPLE 12

N$^4$-(2,3-DIHYDRO-1H-INDEN-5-YL)-2-[4-(2-FLUOROPHENYL)-1-PIPERAZINYL]-N$^6$,N$^6$-DIMETHYL-4,6-PYRIMIDINEDIAMINE: $^1$H NMR (CDCl$_3$) δ 7.34–6.71 (m, 7H), 6.23 (br s, 1H), 5.30 (s, 1H), 3.94 (t, 4H, J=5), 3.11 (t, 4H, J=5), 3.00 (s, 6H), 2.92–2.82 (m, 4H), 2.13–2.01 (m, 2H); $^1$H NMR (CDCl$_3$) δ ESI-MS m/z: 433 (MH$^+$).

EXAMPLE 13

2-[4-(2-FLUOROPHENYL)-1-PIPERAZINYL]-N$^4$-(3-METHOXYPHENYL)-N$^6$,N$^6$-DIMETHYL-4,6-PYRIMIDINEDIAMINE: $^1$H NMR (CDCl$_3$) δ 7.15–7.08 (m, 1H), 7.02–6.95 (m, 1H), 6.94–6.83 (m, 4H), 6.79–6.74 (m, 1H), 6.54–6.47 (m, 1H), 6.32 (br s, 1H), 5.27 (s, 1H), 3.87 (t, 4H, J=5.4), 3.69 (s, 3H), 3.04 (t, 4H, J=5.4), 2.91 (s, 6H); ESI-MS m/z: 423 (MH$^+$).

EXAMPLE 14

N$^4$-{3-CHLORO-4-[(TRIFLUOROMETHYL) SULFANYL]PHENYL}-2-[4-(2-FLUOROPHENYL)-1-PIPERAZINYL]-N$^6$,N$^6$-DIMETHYL-4,6-PYRIMIDINEDIAMINE: $^1$H NMR (CDCl$_3$) δ 7.88–7.85 (m, 1H), 7.62 (d, 1H, J=7.5), 7.48 (d, 1H, J=7.5), 7.12–6.91 (m, 2H), 6.80 (m, 1H), 6.55 (dd, 1H, J=3.3, 8,7), 6.36 (br s, 1H), 5.27 (s, 1H), 3.96 (t, 4H, J=5.0), 3.15 (t, 4H, J=5.0), 3.01 (s, 6H); ESI-MS m/z: 527 (MH$^+$).

EXAMPLE 15

2-[4-(4-CHLOROPHENYL)-1-PIPERAZINYL]-N$^4$-(3-METHOXYPHENYL)-N$^6$,N$^6$-DIMETHYL-4,6-PYRIMIDINEDIAMINE: $^1$H NMR (CDCl$_3$) δ 7.28–7.18 (m, 2H), 7.01–6.97 (m, 1H), 6.96–6.83 (m, 3H), 6.63–6.56 (m, 2H), 6.29 (s, 1H), 5.37 (s, 1H), 3.92 (t, 4H, J=5.2), 3.78 (s, 3H), 3.18 (t, 4H, J=5.8), 3.00 (s, 6H); ESI-MS m/z: 439 (MH$^+$).

EXAMPLE 16

2-[4-(3-CHLOROPHENYL)-1-PIPERAZINYL]-N$^4$-(3,4-DICHLOROPHENYL)-N$^6$,N$^6$-DIMETHYL-4,6-PYRIMIDINEDIAMINE: $^1$H NMR (CDCl$_3$) δ 7.73–7.65 (m, 1H), 7.22–7.11 (m, 2H), 6.93 (t, 1H, J=2.4), 6.86–6.80 (m, 1H), 6.76 (d, 1H, J=2.4), 6.51 (dd, 1H, J=3.2, 8.9 HZ), 6.19 (s, 1H), 5.20 (s, 1H), 3.92 (t, 4H, J=6.5), 3.24 (t, 4H, J=6.5), 3.01 (s, 6H); ESI-MS m/z: 477 (MH$^+$).

EXAMPLE 17

2-[4-(2-CHLOROPHENYL)-1-PIPERAZINYL]-N$^4$-(3,4-DIMETHYLPHENYL)-N$^6$,N$^6$-DIMETHYL-4,6-PYRIMIDINEDIAMINE: $^1$H NMR (CDCl$_3$) δ 7.42–7.35 (m, 1H), 7.25–7.15 (m, 1H), 7.17–6.84 (m, 4H), 6.65–6.49 (m, 1H), 6.23 (br s, 1H), 5.30 (s, 1H), 3.95 (t, 4H, J=5.2), 3.10 (t, 4H, J=5.2), 3.00 (s, 6H), 2.24 (s, 3H), 2.23 (s, 3H); ESI-MS m/z: 437 (MH$^+$).

EXAMPLE 18

N$^4$-(4-CYCLOHEXYLPHENYL)-2-[4-(2-FLUOROPHENYL)-1-PIPERAZINYL]-N$^6$,N$^6$-DIMETHYL-4,6-PYRIMIDINEDIAMINE: $^1$H NMR (CDCl$_3$) δ 7.30–6.89 (m, 8H), 6.31 (br s, 1H), 5.31 (s, 1H), 3.95 (t, 4H, 5.3), 3.12 (t, 4H, 5.3), 3.00 (s, 6H), 2.53–2.41 (m, 1H), 1.93–1.67 (m, 4H), 1.35–1.15 (m, 6H); ESI-MS m/z: 475 (MH$^+$).

EXAMPLE 19

N$^4$-(3,4-DIMETHYLPHENYL)-2-[4-(2-FLUOROPHENYL)-1-PIPERAZINYL]-N$^6$,N$^6$-DIMETHYL-4,6-PYRIMIDINEDIAMINE: $^1$H NMR (CDCl$_3$) δ 7.12–6.90 (m, 7H), 6.25 (s, 1H), 5.29 (s, 1H), 3.95 (t, 4H, J=5.6), 3.11 (t, 4H, J=5.7), 2.99 (s, 6H), 2.04 (s, 6H); ESI-MS m/z: 421 (MH$^+$).

EXAMPLE 20

2-[4-(3-CHLOROPHENYL)-1-PIPERAZINYL]-N$^4$-{3-CHLORO-4-[(TRIFLUOROMETHYL) SULFANYL] PHENYL}-N$^6$,N$^6$-DIMETHYL-4,6-PYRIMIDINEDIAMINE: $^1$H NMR (CDCl$_3$) δ 7.63 (d, 1H, J=3.9), 7.49 (d, 1H, J=9.1) 7.24 (d, 1H, J 2.4), 7.19 (t, 1H, J=8.2), 6.94 (t, 1H, J=2.5), 6.87–6.79 (m, 1H), 6.55 (dd, 1H, J=2.4, 8.2), 6.34 (3, 1H), 5.27 (s, 1H), 3.93 (t, 4H, J=5.8), 3.26 (t, 4H, J=6.1), 3.01 (s, 6H); ESI-MS m/z: 543 (MH$^+$).

EXAMPLE 21

2-[4-(2-CHLOROPHENYL)-1-PIPERAZINYL]-N$^4$-(3,4-DICHLOROPHENYL)-N$^6$,N$^6$-DIMETHYL-4,6-PYRIMIDINEDIAMINE: $^1$H NMR (CDCl$_3$) δ 7.72–7.64 (m, 1H), 7.42–6.95 (m, 4H), 6.80–6.72 (m, 1H), 6.55–6.46 (m, 1H), 6.18 (br s, 1H), 5.22 (s, 1H), 3.96 (t, 4H, J=5.2), 3.11 (t, 4H, J=5.2), 3.02 (s, 6H); ESI-MS m/z: 477 (MH$^+$).

EXAMPLE 22

2-[4-(2-CHLOROPHENYL)-1-PIPERAZINYL]-N$^4$-{3-CHLORO-4-[(TRIFLUOROMETHYL) SULFANYL] PHENYL}-N$^6$,N$^6$-DIMETHYL-4,6-PYRIMIDINE DIAMINE: $^1$H NMR (CDCl$_3$) δ 7.86 (d, 1H, J=1.5), 7.72–7.59 (m, 2H), 7.42–7.35 (m, 2H), 7.28 (d, 2H, J=9.1), 6.38 (br s, 1H), 5.26 (s, 1H), 4.14–3.92 (m, 4H, J=6.1), 3.16–3.08 (t, 4H, J=6.1), 3.00 (s, 6H); ESI-MS m/z: 543 (MH$^+$).

EXAMPLE 23

2-[4-(4-CHLOROPHENYL)-1-PIPERAZINYL]-N$^4$-(3,4-DIMETHYLPHENYL)-N$^6$,N$^6$-DIMETHYL-4,6-PYRIMIDINEDIAMINE: $^1$H NMR (CDCl$_3$) δ 7.22 (d, 4H, J=8.2), 7.07 (m, 1H), 6.89 (d, 2H, J=8.3), 6.18 (br s, 1H), 5.30 (s, 1H), 3.92 (t, 4H, J=6.2), 3.19 (t, 4H, J=6.2), 3.00 (s, 6H), 2,24 (m, 6H); ESI-MS m/z: 437 (MH$^+$).

EXAMPLE 24

N$^4$-[3-(BENZYLOXY)PHENYL]-2-[4-(2-FLUOROPHENYL)-1-PIPERAZINYL]-N$^6$,N$^6$-DIMETHYL-4,6-PYRIMIDINEDIAMINE: $^1$H NMR (CDCl$_3$) δ 7.47–7.16 (m, 6H), 7.12–6.85 (m, 6H), 6.70–6.63 (m, 1H), 6.32 (s, 1H), 5.35 (s, 1H), 5.04 (s, 2H), 3.96 (t, 4H, J=5.5), 3.11 (t, 4H, J=5.5), 3.00 (s, 6H); ESI-MS m/z: 499 (MH$^+$).

EXAMPLE 25

$N^4$-[3-(BENZYLOXY)PHENYL]-2-[4-(2-CHLOROPHENYL)-1-PIPERAZINYL]-$N^6$,$N^6$-DIMETHYL-4,6-PYRIMIDINEDIAMINE: $^1$H NMR (CDCl$_3$) δ 7.46–7.29 (m, 6H), 7.25–7.18 (m, 2H), 7.11–6.95 (m, 3H), 6.91–6.86 (m, 1H), 6.69–6.64 (m, 1H), 6.27 (s, 1H), 5.36 (s, 1H), 5.06 (s, 2H), 3.97 (t, 4H, J=5.2), 3.10 (t, 4H, J=5.2), 3.00 (s, 6H); ESI-MS m/z: 515 (MH$^+$).

EXAMPLE 26

$N^4$-[3-(ISOPROPYLAMINO)-4-METHYLPHENYL]-$N^6$,$N^6$-DIMETHYL-2-[4-(2-PYRIDINYL)-1-PIPERAZINYL]-4,6-PYRIMIDINEDIAMINE: $^1$H NMR (CDCl$_3$) O8.24–8.20 (m, 1H), 7.53–7.47 (m, 1H), 6.98 (d, 1H, J=9), 6.72–6.49 (m, 4H), 6.24 (s, 1H), 5.40 (s, 1H), 4.13 (q, 1H, J=7), 3.93–3.88 (m, 4H), 3.63–3.59 (m, 4H), 3.00 (s, 6H), 2.09 (s, 3H), 1.25 (d, 6H); ESI-MS m/z: 447 (MH$^+$)

EXAMPLE 27

$N^4$-[3-(BENZYLOXY)PHENYL]-2-[4-(3-CHLOROPHENYL)-1-PIPERAZINYL]-$N^6$,$N^6$-DIMETHYL-4,6-PYRIMIDINEDIAMINE: $^1$H NMR (CDCl$_3$) δ 7.61–7.27 (m, 5H), 7.23–7.11 (m, 2H), 7.09–7.02 (m, 1H), 6.93–6.78 (m, 2H), 6.73–6.62 (m, 2H), 6.43–6.27 (m, 2H), 5.04 (s, 1H), 5.01 (s, 2H), 3.92 (t, 4H, J 5.2), 3.14 (t, 4H, J=5.2), 3.00 (s, 6H); ESI-MS m/z: 515 (MH$^+$).

EXAMPLE 28

$N^4$-[3-(DIMETHYLAMINO)PHENYL]-$N^6$,$N^6$-DIMETHYL-2-[4-(2-PYRIDINYL)-1-PIPERAZINYL]-4,6-PYRIMIDINEDIAMINE: $^1$H NMR (CDCl$_3$) δ 8.23–8.20 (m, 1H), 7.49 (dt, 1H, J=1.8, 7.4), 7.17 (t, 1H, J=8.0), 6.77 (t, 1H, J=1.8), 6.68 (d, 1H, J=8.6), 6.66–6.60 (m, 2H), 6.45 (dd, 1H, J=8.3, 2.7), 6.32 (br s, 1H), 5.43 (s, 1H), 3.91 (t, 4H, J=5.1), 3.60 (t, 4H, J=5.1), 3.01 (s, 6H), 2.95 (s, 6H); ESI-MS m/z: 419 (MH$^+$).

EXAMPLE 29

$N^4$-(3,4-DICHLOROPHENYL)-2-[4-(2-FLUOROPHENYL)-1-PIPERAZINYL]-$N^6$,$N^6$-DIMETHYL-4,6-PYRIMIDINEDIAMINE: $^1$H NMR (CDCl$_3$) δ 7.69 (m, 1H), 7.40–7.30 (m, 1H), 7.22–6.88 (m, 3H), 6.76 (d, 1H, J=3.1), 6.51 (dd, 1H, J=2.6, 7.8), 6.18 (s, 1H), 5.22 (s, 1H), 3.95 (t, 4H, J=5.2), 3.14 (t, 4H, J=5.2), 3.01 (s, 6H); ESI-MS m/z: 461 (MH$^+$).

EXAMPLE 30

2-[4-(4-CHLOROPHENYL)-1-PIPERAZINYL]-$N^4$-{3-CHLORO-4-[TRIFLUOROMETHYL) SULFANYL]PHENYL}-$N^6$,$N^6$-DIMETHYL-4,6-PYRIMIDINEDIAMINE: $^1$H NMR (CDCl$_3$) 6 7.62 (d, 2H, J=8.1), 7.23 (d, 1H, J=8.1), 6.89 (d, 2H, J=9.3), 6.80 (d, 1H, J=2.4), 6.55 (dd, 1H, J=2.3, 8.1), 6.38 (br s, 1H), 5.26 (s, 1H), 3.94 (t, 4H), 3.21 (t, 4H), 3.05 (s, 6H); ESI-MS m/z: 543 (MH$^+$).

EXAMPLE 31

$N^4$-[3-(BENZYLOXY)PHENYL]-2-[4-(4-CHLOROPHENYL)-1-PIPERAZINYL]-$N^6$,$N^6$-DIMETHYL-4,6-PYRIMIDINEDIAMINE: $^1$H NMR (CDCl$_3$) δ 7.51–7.28 (m, 5H), 7.24–7.18 (m, 2H), 7.10–7.03 (m, 1H), 6.92–6.81 (m, 1H), 6.75–6.62 (m, 1H), 6.45–6.28 (m, 2H), 6.25 (s, 1H), 5.34 (s, 1H), 5.05 (s, 2H), 3.92 (t, 4H, J=5.9), 3.17 (t, 4H, J=5.9), 3.00 (s, 6H); ESI-MS m/z: 515 (MH$^+$).

EXAMPLE 32

2-[4-(3-CHLOROPHENYL)-1-PIPERAZINYL]-$N^4$-(3,4-DIMETHYLPHENYL)-$N^6$,$N^6$-DIMETHYL-4,6-PYRIMIDINEDIAMINE: $^1$H NMR (CDCl$_3$) δ 7.20–6.97 (m, 2H), 6.93–6.76 (m, 2H), 6.65–6.60 (m, 1H), 6.53 (m, 1H, J=6.9), 6.22 (br s, 1H), 5.30 (s, 1H), 3.90 (t, 4H, J=6.1), 3.22 (t, 4H, J=6.1), 3.00 (s, 6H), 2.23 (m, 6H); ESI-MS m/z: 437 (MH$^+$).

EXAMPLE 33

2-(4-BENZYL-1-PIPERAZINYL)-$N^4$-[3-(ETHYLAMINO)PHENYL]$N^6$,$N^6$-DIMETHYL-4,6-PYRIMIDINEDIAMINE: $^1$H NMR (CDCl$_3$) δ 7.37–7.27 (m, 5H), 7.08 (t, 1H), 6.63–6.27 (m, 2H), 6.19 (s, 1H), 5.36 (s, 1H), 3.82–3.77 (m, 4H), 3.54 (s, 2H), 3.14 (q, 2H, J=7), 3.00 (s, 6H), 2.53–2.46 (m, 4H), 1.24 (t, 3H, J=7); ESI-MS m/z: 432 (MH$^+$)

EXAMPLE 34

$N^4$-[3-(BENZYLOXY)PHENYL]-2-[CIS-2,6-DIMETHYLMORPHOLINYL]-$N^6$,$N^6$-DIMETHYL-4,6-PYRIMIDINEDIAMINE: $^1$H NMR (CDCl$_3$) δ 7.49–7.29 (m, 5H), 7.20 (t, 1H, J=8.0), 7.09 (t, 1H, J=2.0), 6.84 (dd, 1H, J=8.2, 1.6), 6.66 (dd, 1H, J=8.7, 2.2), 6.27 (s, 1H), 5.34 (s, 1H), 5.05 (s, 2H), 4.53 (d, 2H, J=13.8), 3.75–3.59 (m, 2H), 3.00 (s, 6H), 2.52 (dd, 2H, J=13.0, 10.7), 1.22 (d, 6H, J=6.4); ESI-MS m/z: 434 (MH$^+$).

EXAMPLE 35

$N^4$-[3-(BENZYLOXY)PHENYL]-$N^2$,$N^6$,$N^6$-TRIMETHYL-$N^2$-(TETRAHYDRO-2-FURANYLMETHYL)-2,4,6-PYRIMIDINETRIAMINE: $^1$H NMR (CDCl$_3$) δ 7.54–7.29 (m, 5H), 7.24–7.13 (m, 2H), 6.89 (dd, 1H, J=8.3, 2.1), 6.63 (dd, 1H, J=8.2, 2.4), 6.24 (br s, 1H), 5.27 (s, 1H), 5.05 (s, 2H), 4.29–4.15 (m, 1H), 3.93–3.82 (2m, 2H), 3.72 (q, 1H, J=6.3), 3.58 (dd, 1H, J=14.0, 6.0), 3.20 (s, 3H), 2.99 (s, 6H), 2.05–1.55 (m, 4H); ESI-MS m/z: 434 (MH$^+$).

EXAMPLE 36

$N^4$-[3-(BENZYLOXY)PHENYL]-$N^6$,$N^6$-DIMETHYL-2-(1-PIPERIDINYL)-4,6-PYRIMIDINEDIAMINE: $^1$H NMR (CDCl$_3$) δ 7.55–7.30 (m, 6H), 7.19 (t, 1H, J=8.0), 7.15 (s, 1H), 6.85 (d, 1H, J=8.1), 6.64 (d, 1H, J=8.2), 6.24 (s, 1H), 5.29 (s, 1H), 5.05 (s, 2H), 3.93–3.65 (m, 4H), 3.00 (s, 6H), 1.82–1.51 (m, 6H); ESI-MS m/z: 404 (MH$^+$).

EXAMPLE 37

$N^4$-[3-(BENZYLOXY)PHENYL]-$N^6$,$N^6$-DIMETHYL-2-(1-PYRROLIDINYL)-4,6-PYRIMIDINEDIAMINE: $^1$H NMR (CDCl$_3$) δ 7.55–7.29 (m, 6H), 7.20 (t, 1H, J=8.4), 6.94–6.85 (m, 1H), 6.74–6.63 (m, 1H), 6.31 (br s, 1H), 5.30 (s, 1H), 5.06 (s, 2H) 3.59 (br s, 4H), 3.00 (s, 6H), 1.93 (br s, 4H); ESI-MS m/z: 390 (MH$^+$).

EXAMPLE 38

$N^4$-[3-(BENZYLOXY)PHENYL]-2-(3,5-DIMETHYL-1-PIPERIDINYL)-$N^6$,$N^6$-DIMETHYL-4,6-PYRIMIDINEDIAMINE: $^1$H NMR (CDCl$_3$) δ 7.56–7.29 (m, 5H), 7.19 (t, 1H, J=8.0), 7.12 (d, 1H, J=8.6), 6.85 (d, 1H, J=8.0), 6.64 (d, 1H, J=7.8), 6.25 (br s, 1H), 5.29 (s, 1H), 5.05 (s, 2H), 4.73 (d, 2H, J=12.3), 2.99 (s, 6H), 2.22 (t, 2H, J=12.2), 1.98–1.91 (m, 1H), 1.79 (d, 1H, J=13.1), 1.78–1.53 (m, 2H), 0.95 (d, 3H, J=6.9), 0.91 (d, 3H, J=6.6); ESI-MS m/z: 432 (MH$^+$).

EXAMPLE 39

N²-BENZYL-N⁴,N⁴-DIMETHYL-N⁶-(4-METHYLPHENYL)-2,4,6-PYRIMIDINE TRIAMINE: ¹H NMR (CDCl₃) δ 7.49 (d, 1H, J=8.5), 7.41–7.20 (m, 3H), 7.16 (d, 2H, J=9), 7.10 (d, 2H, J=8.5), 7.05 (d, 1H, J=7.5), 6.29 (br s, 1H), 5.83 (br s, 1H), 5.29 (s, 1H), 4.62–4.56 (m, 2H), 3.00 (s, 6H), 2.31 (s, 3H); ESI-MS m/z:

EXAMPLE 40

2-(4-BENZYL-1-PIPERAZINYL)-N⁴-[3-(ETHYLAMINO)-4-METHYLPHENYL]-N⁶,N⁶-DIMETHYL-4,6-PYRIMIDINEDIAMINE: ¹H NMR (CDCl₃) δ 7.37–7.30 (m, 5H), 6.96 (d, 1H, J=8), 6.62 (d, 1H, J=2), 6.51 (dd, 1H, J=8, 2), 6.19 (s, 1H), 5.36 (s, 1H), 3.79 (t, 4H, J=5), 3.55 (s, 2H), 3.15 (q, 2H, J=7), 2.97 (s, 6H), 2.48 (t, 4H, J=5), 2.10 (s, 3H), 1.29 (t, 3H, J=7); ESI-MS m/z: 446 (MH⁺)

EXAMPLE 41

N-[3-(BENZYLOXY)PHENYL]-N⁶,N⁶-DIMETHYL-2-[4-(2-PYRIMIDINYL)-1-PIPERAZINYL]-4,6-PYRIMIDINEDIAMINE: ¹H NMR (CDCl₃) δ 8.31 (d, 2H, J=4.8), 7.47–7.29 (m, 5H), 7.21 (t, 1H, J=8.5), 7.03 (t, 1H, J=1.8), 6.96–6.60 (m, 2H), 6.50 (t, 1H, J=5.0), 6.27 (br s, 1H), 5.36 (s, 1H), 5.07 (s, 2H), 3.95–3.82 (m, 8H), 3.02 (s, 6H); ESI-MS m/z: 483 (MH⁺).

EXAMPLE 42

N⁴-[3-(BENZYLOXY)PHENYL]-2-(2,3-DIHYDRO-1H-INDOL-1-YL)-N⁶,N⁶-DIMETHYL-4,6-PYRIMIDINEDIAMINE: ¹H NMR (CDCl₃) δ 7.65 (d, 1H, J=8), 7.46–7.28 (m, 3H), 7.25–7.08 (m, 9H), 6.36 (br s, 1H), 5.45 (s, 2H), 5.28 (s, 1H), 5.07–5.02 (m, 2H), 4.24 (t, 2H, J=10), 3.0 (s, 6H);ESI-MS m/z: 438 (MH⁺).

EXAMPLE 43

N-(3,4-DICHLOROPHENYL)-2,6-BIS[4-(2-PYRIDINYL)-1-PIPERAZINYL]-4-PYRIMIDINAMINE: ¹H NMR (CDCl₃) δ 8.23–8.18 (m, 2H), 7.73 (d, 1H, J=2.6), 7.54–7.46 (m, 2H), 7.34 (d, 1H, J=8.7), 7.15 (dd, 1H, J=8.8, 2.6), 6.73–6.62 (m, 4H), 6.29 (s, 1H), 5.31 (s, 1H), 3.91 (t, 4H, J=5.1), 3.74–3.58 (m, 12H); ESI-MS m/z: 562 (MH⁺).

EXAMPLE 44

N⁴-[2-(DIETHYLAMINO)-4-METHYLPHENYL]-N⁶,N⁶-DIMETHYL-2-[4-(2-PYRIDINYL)-1-PIPERAZINYL]-4,6-PYRIMIDINEDIAMINE: ¹H NMR (CDCl₃) δ 8.16–8.12 (m, 1H), 7.87 (d, 1H, J=4.5), 7.46–7.37 (m, 3H), 6.86–6.81 (m, 2H), 5.23 (s, 1H), 3.86 (t, 4H, J=5.7), 3.56 (t, 4H, J=5.7), 2.96 (s, 6H), 2.16 (s, 3H), 2.10–2.09 (m, 4H), 0.95–0.85 (m, 6H); ESI-MS m/z: 423 (MH⁺).

EXAMPLE 45

N⁴-[2-(ISOPROPYLAMINO)-4-METHYLPHENYL]-N⁶,N⁶-DIMETHYL-2-[4-(2-PYRIDINYL)-1-PIPERAZINYL]-4,6-PYRIMIDINEDIAMINE: ¹H NMR (CDCl₃) δ 8.22–8.2 (m, 1H), 7.52–7.47 (m, 1H), 7.01 (d, 1H, J=8), 6.69 (d, 1H, J=9), 6.63 (dd, 1H, J=8.5), 6.52 (s, 1H), 6.45 (d, 1H, J=8), 5.66 (s, 1H), 4.8 (s, 1H), 3.91–3.89 (m, 4H), 3.68–3.6 (m, 5H), 2.94 (s, 6H), 2.32 (s, 3H), 1.17 (d, 6H, J=15); ESI-MS m/z: 447 (MH⁺)

EXAMPLE 46

N⁴,N⁴-DIMETHYL-N⁶-(4-METHYLPHENYL)-2-{4-[1-OXIDO-3-(TRIFLUOROMETHYL)-2-PYRIDINYL]-1-PIPERAZINYL}-4,6-PYRIMIDINEDIAMINE: ¹H NMR (CDCl₃) δ 7.55 (s, 1H), 7.22–7.08 (m, 6H), 6.21 (br s, 1H), 5.28 (s, 1H), 3.98–3.87 (m, 4H), 3.76–3.54 (m, 4H), 2.99 (s, 6H), 2.33 (s, 3H) ESI-MS m/z: 474 (MH⁺).

EXAMPLE 47

N⁴-(1-ETHYL-1H-INDOL-6-YL)-N⁶,N⁶-DIMETHYL-2-[4-(2-PYRIDINYL)-1-PIPERAZINYL]-4,6-PYRIMIDINEDIAMINE: ¹H NMR (CDCl₃) δ 8.17–8.13 (m, 1H), 7.49–7.29 (m, 3H), 7.03–6.89 (m, 2H), 6.64–6.55 (m, 2H), 6.46–6.38 (m, 1H), 6.15 (s, 1H), 5.29 (s, 1H), 4.07 (q, 2H, J=6), 3.89–3.80 (m, 4H), 3.60–3.53 (m, 4H), 2.93 (s, 6H), 1.39 (t, 3H, J=6); ESI-MS m/z: 443 (MH⁺).

EXAMPLE 48

(±)-N⁴-[3-(BENZYLOXY)PHENYL]-2-(TRANS-2,6-DIMETHYL MORPHOLINYL)-N⁶,N⁶-DIMETHYL-4,6-PYRIMIDINEDIAMINE: ¹H NMR (CDCl₃) δ 7.45–7.3 (m, 5H), 7.2 (t, 1H, J=8), 7.10–7.00 (m, 1H), 6.86 (dd, 1H, J=9,3), 6.66 (dd, 1H, J=9, 3), 6.29 (s, 1H), 5.32 (s, 1H), 5.04 (s, 2H), 4.10–4.03 (m, 2H), 3.85 (dd, 2H, J=13, 4), 3.49 (dd, 2H, J=13, 6), 2.99 (s, 6H), 1.24 (d, 6H, J=6); ESI-MS m/z: 437 (MH⁺).

EXAMPLE 49

N⁴-{3-[BENZYL(METHYL)AMINO]-4-METHYLPHENYL}-2-[CIS-2,6-DIMETHYIMORPHOLINYL]-N⁶,N⁶-DIMETHYL-4,6-PYRIMIDINEDIAMINE: ¹H NMR (CDCl₃) δ 7.40–7.31 (m, 5H), 7.18–7.10 (m, 2H), 6.85 (dd, 1H, J=8.2), 6.20 (s, 1H), 4.58–4.50 (m, 2H), 4.02 (s, 2H), 3.69–3.61 (m, 2H), 3.00 (s, 6H), 2.59 (s, 3H), 2.52 (t, 2H, J=11), 2.36 (S, 3H,), 1.24 (d, 6H, J=6); ESI-MS m/z: 461(MH⁺).

EXAMPLE 50

N⁴-[3-(SEC-BUTYLAMINO)-4-METHYLPHENYL]-2-[CIS-2,6-DIMETHYL MORPHOLINYL]-N⁶,N⁶-DIMETHYL-4,6-PYRIMIDINEDIAMINE: ¹H NMR (CDCl₃) δ 7.10 (d, 1H, J=8.2), 7.05 (d, 1H, J=8.2), 6.90 (d, 1H, J=7.8), 6.47 (d, 1H, J=2.0), 6.41 (dd, 1H, J=7.8, 2.0), 6.12 (br s, 1H), 5.32 (s, 1H), 4.47 (d, 2H, J=11.7), 3.62–3.53 (m, 2H), 3.33–3.27 (m, 2H), 2.92 (s, 6H), 2.45 (t, 2H, J=12.5), 2.01 (s, 3H), 1.24–1.10 (m, 11H), 0.88 (t, 1H, J=7.0); ESI-MS m/z: 413 (MH⁺).

EXAMPLE 51

N⁴-(3,4-DICHLOROPHENYL)-2-(CIS-2,6-DIMETHYLMORPHOLINYL)-N⁶,N⁶-DIMETHYL-4,6-PYRIMIDINEDIAMINE: ¹H NMR (CDCl₃) δ 7.82 (d, 1H, J=3.1), 7.31 (d, 1H, J=8.5), 7.04 (dd, 1H, J=8.5, 3.1), 6.18 (br s, 1H), 5.19 (s, 1H), 4.51 (dd, 2H, J=13.8, 2.0), 3.71–3.62 (m, 2H), 3.02 (s, 6H), 2.55 (dd, 2H, J=13.2, 10.5), 1.25 (d, 6H, J=4.7); ESI-MS m/z: 396 (MH⁺).

EXAMPLE 52

2-(CIS-2,6-DIMETHYLMORPHOLINYL)-N-(4-METHYLPHENYL)-6-[4-(2-PYRIMIDINYL)-1-PIPERAZINYL]-4-PYRIMIDINAMINE: ¹H NMR (CDCl₃) δ 8.32 (d, 2H, J=4.8), 7.17 (d, 2H, J=8.7), 7.14 (d, 2H, J=8.7), 6.51 (t, 1H, J=4.9), 6.24 (br s, 1H), 5.37 (s, 1H), 4.51 (dd, 2H, J=12.9, 1.5), 3.89–3.74 (m, 4H), 3.70–3.62 (m, 2H), 3.59 (t, 4H, J=5.1), 2.53 (dd, 2H, J=13.1, 10.4), 2.34 (s, 3H), 1.28–1.22 (m, 6H); ESI-MS m/z: 461 (MH⁺).

EXAMPLE 53

1-[2-(4-BENZYL-1-PIPERAZINYL)-6-(3,4-DICHLOROANILINO)-4-PYRIMIDINYL]-4-PIPERIDINONE: $^1$H NMR (CDCl$_3$) δ 7.67 (d, 1H, J=2.5), 7.38–7.29 (m, 5H), 7.32 (s, 1H), 7.14 (dd, 1H, J=8.7, 2.7), 6.26 (br s, 1H), 5.34 (s, 1H), 3.85 (t, 4H, J=6.0), 3.83–3.73 (m, 4H), 3.57 (br s, 2H), 2.48 (m, 8H); ESI-MS m/z: 511 (MH$^+$).

EXAMPLE 54

2-[4-(4-CHLOROPHENYL)-1-PIPERAZINYL]-N-(3,4-DICHLOROPHENYL)-N$^6$,N$^6$-DIMETHYL-4,6-PYRIMIDINEDIAMINE: $^1$H NMR (CDCl$_3$) δ 7.70 (d, 1H, J=3), 7.33 (d, 1H, J=9), 7.22 (d, 2H, J=8), 7.20–7.10 (m, 2H), 6.89 (d, 1H, J=8), 6.13 (br s, 1H), 5.21 (s, 1H), 3.92 (t, 4H, J=5.1), 3.20 (t, 4H, J=5.1), 3.01 (s, 6H); ESI-MS m/z: 478 (MH$^+$).

TABLE II

| Example | Structure | Ki GalR3 (nM) |
|---|---|---|
| 1 | 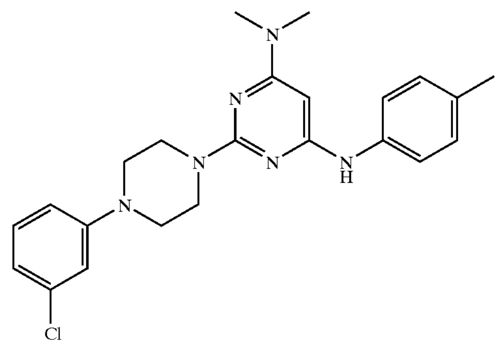 | 65 |
| 2 | 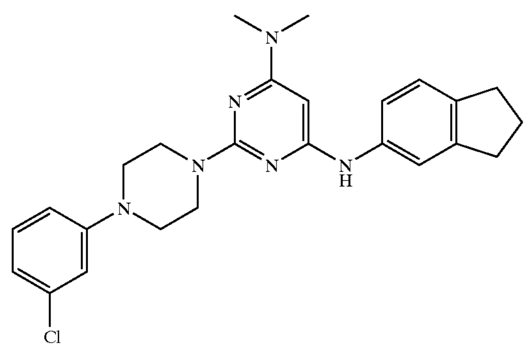 | 34 |
| 3 | 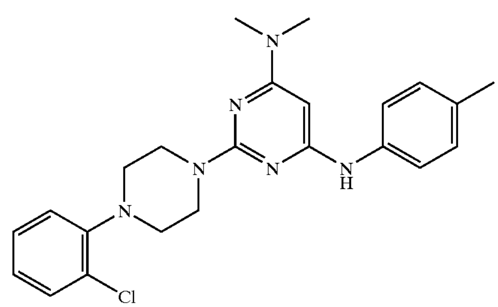 | 29 |
| 4 | 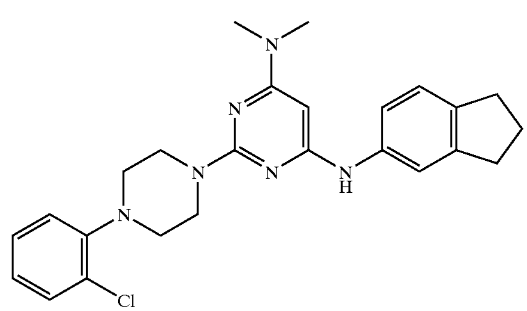 | 54 |

TABLE II-continued

Binding Data

| Example | Structure | Ki GalR3 (nM) |
|---------|-----------|---------------|
| 5 | 2-[4-(2-fluorophenyl)piperazin-1-yl]-N4-(4-methylphenyl)-N6,N6-dimethylpyrimidine-4,6-diamine | 117 |
| 6 | 2-[4-(4-chlorophenyl)piperazin-1-yl]-N4-(2,3-dihydro-1H-inden-5-yl)-N6,N6-dimethylpyrimidine-4,6-diamine | 52 |
| 7 | 2-[4-(4-chlorophenyl)piperazin-1-yl]-N4-(4-methylphenyl)-N6,N6-dimethylpyrimidine-4,6-diamine | 352 |
| 8 | 2-[4-(3-chlorophenyl)piperazin-1-yl]-N4-(3-methoxyphenyl)-N6,N6-dimethylpyrimidine-4,6-diamine | 107 |

TABLE II-continued

Binding Data

| Example | Structure | Ki GalR3 (nM) |
|---|---|---|
| 9 | | 241 |
| 10 | | 47 |
| 11 | | 62 |
| 12 | | 75 |
| 13 | | 93 |

TABLE II-continued
Binding Data
| Example | Structure | Ki GalR3 (nM) |
|---|---|---|
| 14 | 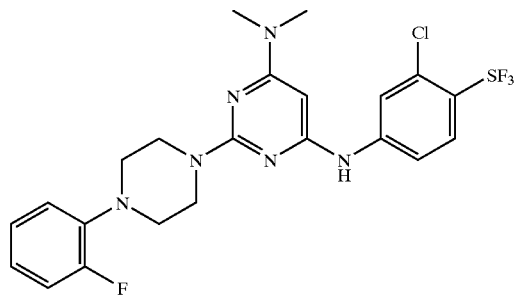 | 158 |
| 15 | 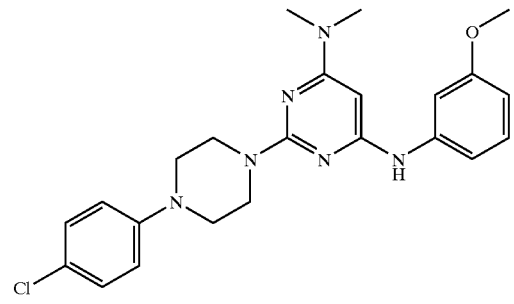 | 88 |
| 16 | 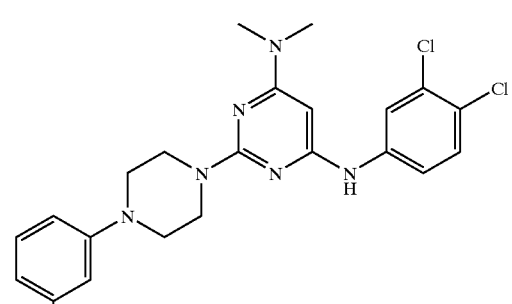 | 34 |
| 17 | 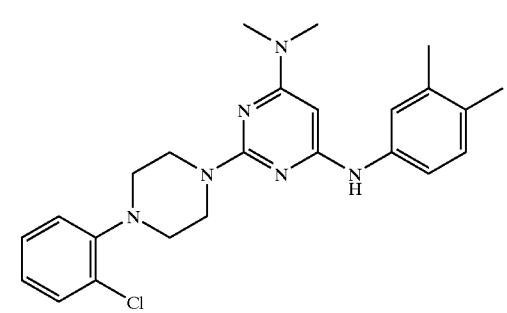 | 57 |

TABLE II-continued

Binding Data

| Example | Structure | Ki GalR3 (nM) |
|---|---|---|
| 18 | 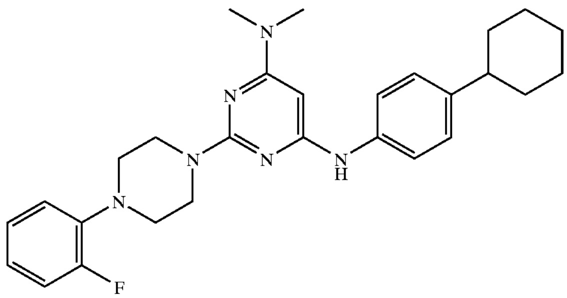 | 46 |
| 19 | 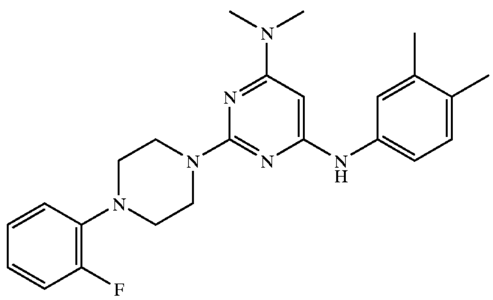 | 118 |
| 20 | 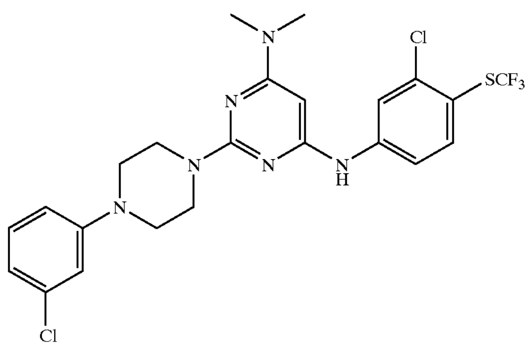 | 318 |
| 21 | 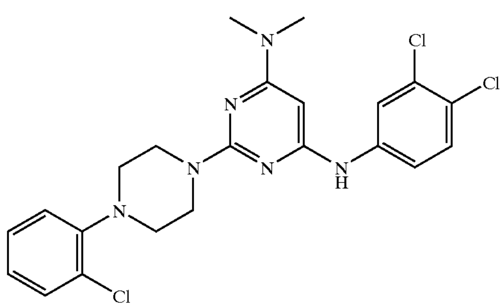 | 63 |
| 22 | 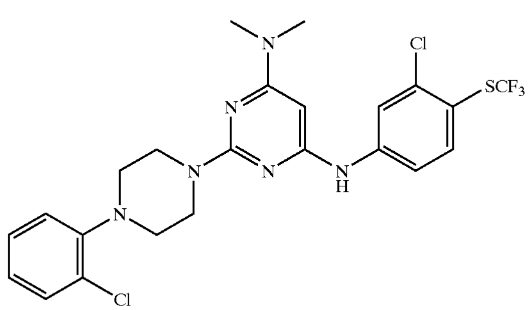 | 182 |

TABLE II-continued

Binding Data

| Example | Structure | Ki GalR3 (nM) |
|---|---|---|
| 23 | | 129 |
| 24 | | 20 |
| 25 | | 16 |
| 26 | | 246 |

TABLE II-continued

Binding Data

| Example | Structure | Ki GalR3 (nM) |
|---------|-----------|---------------|
| 27 | 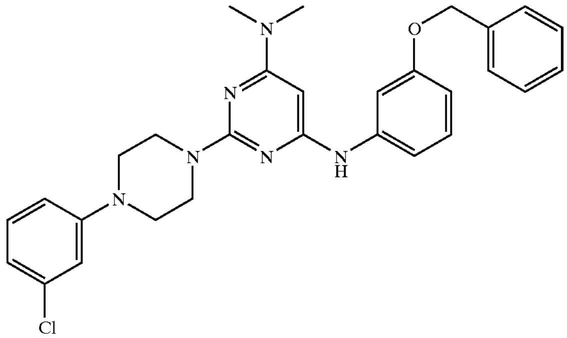 | 28 |
| 28 | 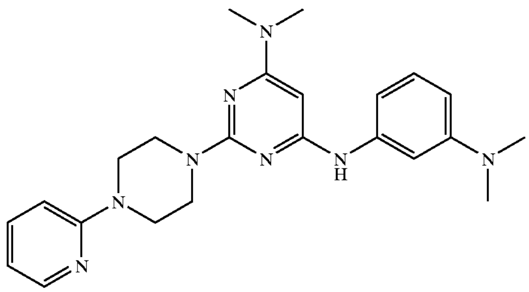 | 417 |
| 29 | 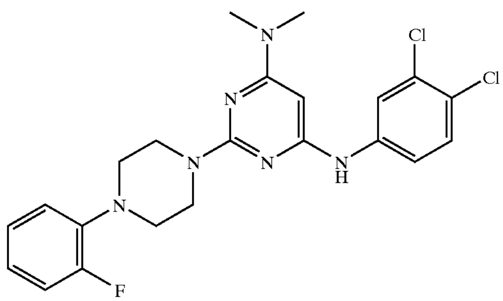 | 27 |
| 30 | 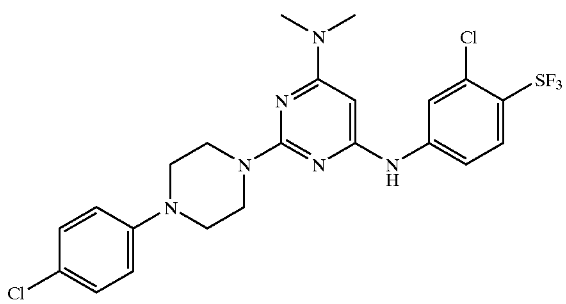 | 138 |
| 31 | 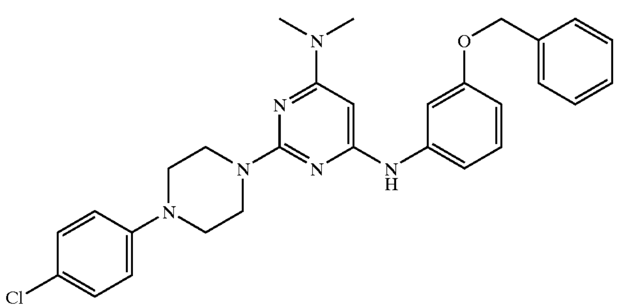 | 26 |

TABLE II-continued
Binding Data
| Example | Structure | Ki GalR3 (nM) |
|---|---|---|
| 32 | 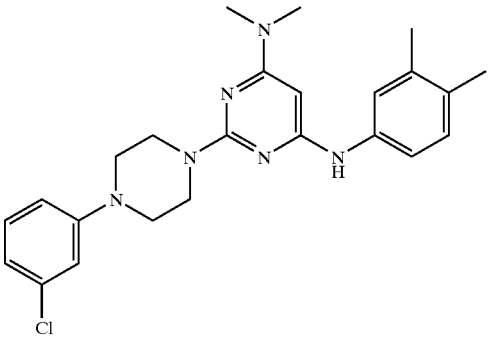 | 97 |
| 33 | 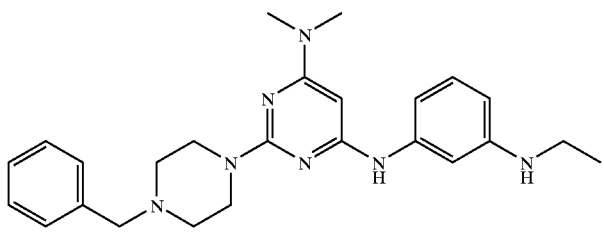 | 942 |
| 34 | 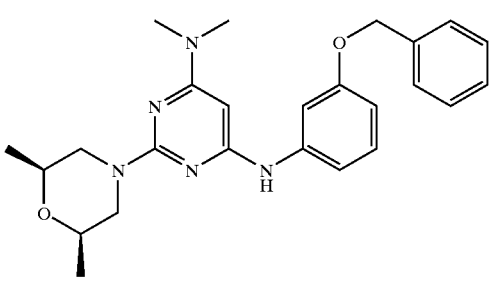 | 32 |
| 35 | 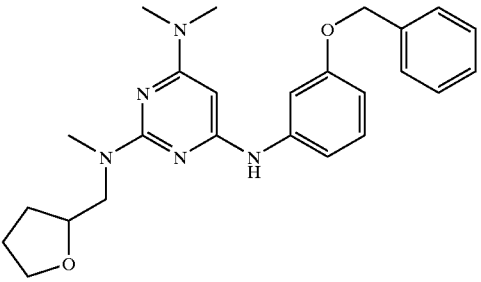 | 42 |
| 36 | 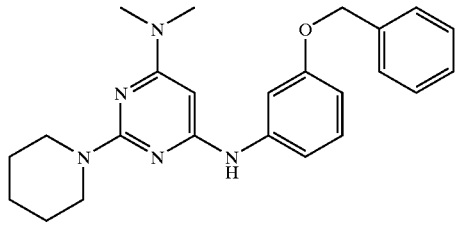 | 23 |

TABLE II-continued

Binding Data

| Example | Structure | Ki GalR3 (nM) |
|---------|-----------|---------------|
| 37 | | 59 |
| 38 | | 15 |
| 39 | | 114 |
| 40 | | 137 |
| 41 | | 14 |
| 42 | | 91 |

TABLE II-continued

Binding Data

| Example | Structure | Ki GalR3 (nM) |
|---|---|---|
| 43 | | 60 |
| 44 | | 314 |
| 45 | | 506 |
| 46 | | 264 |

TABLE II-continued
Binding Data
| Example | Structure | Ki GalR3 (nM) |
|---|---|---|
| 47 | 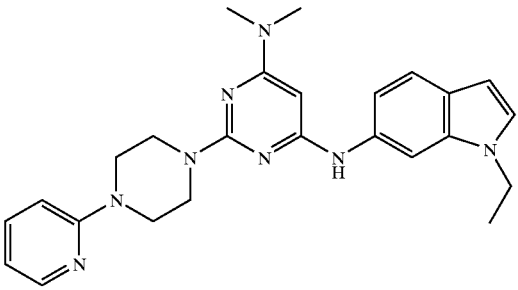 | 351 |
| 48 | 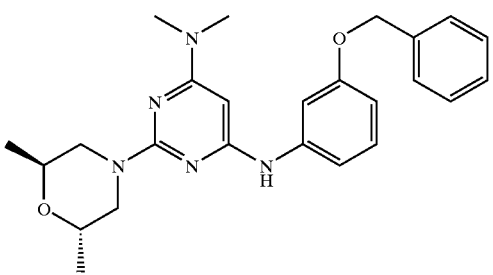 | 30 |
| 49 | 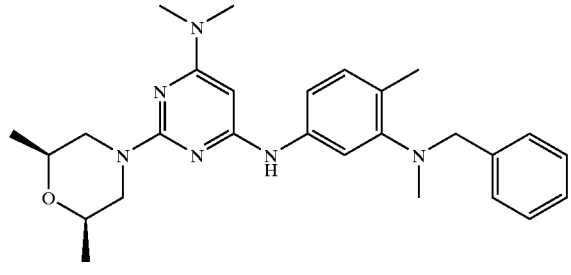 | 103 |
| 50 | 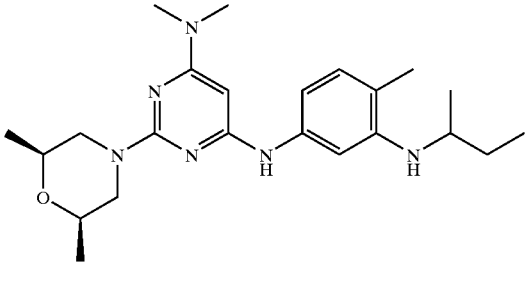 | 312 |
| 51 | 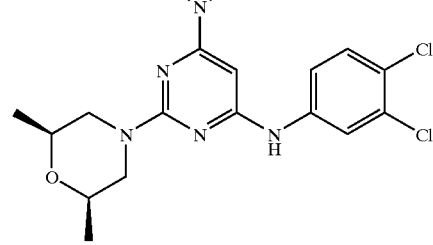 | 81 |

TABLE II-continued

Binding Data

| Example | Structure | Ki GalR3 (nM) |
|---|---|---|
| 52 | 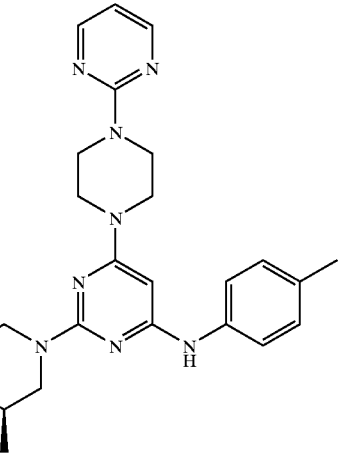 | 117 |
| 53 | 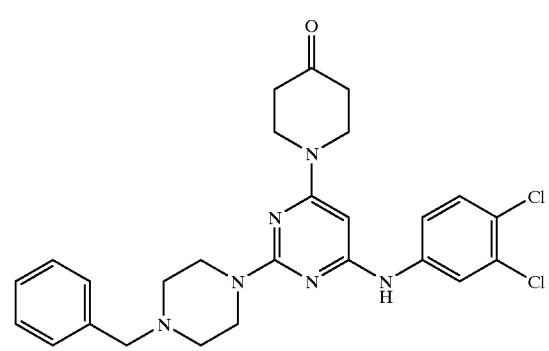 | 36 |
| 54 | 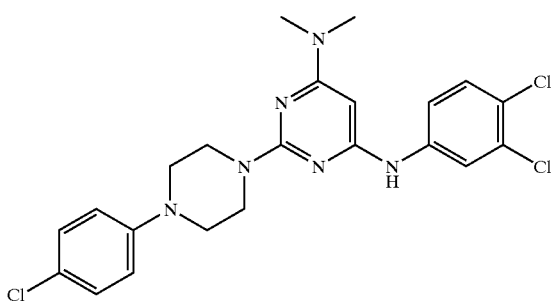 | 150 |

II. Synthetic Methods for General Structures

The examples described in Section I are merely illustrative of the methods used to synthesize GalR3 antagonists. Additional compounds of the invention can be obtained by the general synthetic procedures described herein or by incorporating variations into these methods that would be obvious to someone skilled in the art.

Examples that could be used in place of tetrahydroquinoline in the exemplary procedures to synthesize compounds of this invention include, but are not limited to, indoline, acridine, carbazole, benzazepine or hexahydrocarbazole. Methods for the synthesis of tetrahydroquinolines, indoline, acridine, carbazole, benzazepine and hexahydrocarbazole may be found in the reference section.

It may be necessary to incorporate protection and deprotection strategies for substituents such as amino, amido, carboxylic acid, and hydroxyl groups in the synthetic methods described above to form isatin derivatives. Methods for protection and deprotection of such groups are well-known in the art, and may be found, for example in Green and Wuts, 1991.

III. Oral Compositions

As a specific embodiment of an oral composition of a compound of this invention, 100 mg of one of the compounds described herein is formulated with sufficient finely divided lactose to provide a total amount of about 580 to 590 mg to fill a size 0 hard gel capsule.

IV. Pharmacological Evaluation of Compounds at Cloned GalR3 Receptor

A. Materials and Methods

The binding properties of the compounds of the present invention may be evaluated at one or more cloned receptors or native, tissue-derived transporters, using protocols described below.

Cell Culture

COS-7 cells were grown on 150 mm plates in D-MEM with supplements (Dulbecco's Modified Eagle Medium with 10% bovine calf serum, 4 mM glutamine, 100 units/ml penicillin, 100 μg/ml streptomycin) at 37° C. with 5% $CO_2$. Stock plates of COS-7 cells were trypsinized and split 1:6 every 3–4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin, 100 μg/ml streptomycin) at 37° C. with 5% $CO_2$. Stock plates of 293 cells were trypsinized and split 1:6 every 3–4 days. Mouse fibroblast LM(tk-) cells were grown on 150 mm plates in D-MEM with supplements (Dulbecco's Modified Eagle Medium with 10% bovine calf serum, 4 mM glutamine, 100 units/mL penicillin, 100 μg/mL streptomycin) at 37° C. with 5% $CO_2$. Stock plates of LM(tk-) cells were trypsinized and split 1:10 every 3–4 days. Chinese Hamster Ovary (CHO) cells were grown on 150 mm plates in HAM's F12 medium with (HAM's F-12 with 10% bovine calf serum, 4 mM glutamine, 100 units/mL penicillin, 100 μg/mL streptomycin) at 37° C. with 5% $CO_2$. Stock plates of CHO cells were trypsinized and split 1:8 every 3–4 days.

LM(tk-) cells were stably transfected with the human GalR3 receptor.

Stable Transfection cDNAs for the human and rat GalR3 receptors were transfected with a G-418 resistant gene into the mouse fibroblast LM(tk-) cell line by a calcium phosphate transfection method (Cullen, 1987).

Membrane Harvest

Membranes were harvested from stably transfected LM(tk-) cells. Adherent cells were washed twice in ice-cold phosphate buffered saline (138 mM NaCl, 8.1 mM Na2HPO4, 2.5 mM KCl, 1.2 mM $KH_2PO_4$, 0.9 mM CaCl2, 0.5 mM MgCl2, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM CaCl2, 0.81 mM MgSO4, pH 7.4). Protein concentration was measured by the Bradford method (Bradford, 1976) using Bio-Rad Reagent, with bovine serum albumin as a standard. Membranes were held on ice for up to one hour and used fresh, or flash frozen and stored in liquid nitrogen. Membranes were prepared similarly from CHO cells.

Radioligand Binding Assays and Enzymatic Assays

The methods to obtain the cDNA of the receptors, express said receptors in heterologous systems, and carry out assays to determine binding affinity are described as follows.

Galanin Receptors

Binding assays were performed according to the following published method: human GALR3 (PCT International Publication No. WO 02/060392).

V. In-Vivo Methods

The following in vivo methods are performed to predict the efficacy of GalR3 antagonists for the treatment depression (forced swim test) and anxiety (social interaction test).

Forced Swim Test (FST) in the Rat

Animals

Male Sprague-Dawley rats (Taconic Farms, N.Y.) are to be used in all experiments. Rats are housed 5 per cage and maintained on a 12:12-h light-dark cycle. Rats are handled for 1 minutes each day for 4 days prior to behavioral testing.

Drug Administration

Animals are at be randomly assigned to receive a single i.p. administration of vehicle (2.5% EtOH/2.5% Tween-80), imipramine (positive control; 60 mg/kg), or Test Compound 60 minutes before the start of the 5 minute test period. All injections are given using 1 cc tuberculin syringe with 26⅜ gauge needles (Becton-Dickinson, VWR Scientific, Bridgeport, N.J.). The volume of injection is 1 ml/kg.

Experimental Design

The procedure to be used in this study is similar to that previously described (Porsolt, et al., 1978), except the water depth is 31 cm in this procedure. The greater depth in this test prevents the rats from supporting themselves by touching the bottom of the cylinder with their feet. Swim sessions are conducted by placing rats in individual plexiglass cylinders (46 cm tall×20 cm in diameter) containing 23–25° C. water 31 cm deep. Swim tests are conducted always between 900 and 1700 hours and consisted of an initial 15-minute conditioning test followed 24 hours later by a 5-minute test. Drug treatments are administered 60 minutes before the 5-minute test period. Following all swim sessions, rats are removed from the cylinders, dried with paper towels and placed in a heated cage for 15 minutes and returned to their home cages. All test sessions are videotaped using a color video camera and recorded for scoring later.

Behavioral Scoring

The rat's behavior is rated at 5 second intervals during the 5 minute test by a single individual, who is blind to the treatment condition. Scored behaviors are:

1. Immobility—rat remains floating in the water without struggling and is only making those movements necessary to keep its head above water;
2. Climbing—rat is making active movements with its forepaws in and out of the water, usually directed against the walls;
3. Swimming—rat is making active swimming motions, more than necessary to merely maintain its head above water, e.g. moving around in the cylinder; and
4. Diving—entire body of the rat is submerged.

Data Analysis

The forced swim test data (immobility, swimming, climbing, diving) are subjected to a randomized, one-way ANOVA and post hoc tests conducted using the Newman-Keuls test. The data are analyzed using the GprahPad Prism(v2.01) (GraphPad Software, Inc., San Diego, Calif.). All data are presented as means±S.E.M. All data are presented as means±S.E.M.

Forced Swim Test (FST) in the Mouse

Animals

DBA/2 mice (Taconic Farms, N.Y.) are used in all experiments. Animals are housed 5 per cage in a controlled environment under a 12:12 hour light:dark cycle. Animals are handled 1 min each day for 4 days prior to the experiment. This procedure included a mock gavage with a 1.5 inch feeding tube.

Drug Administration

Animals are randomly assigned to receive a single administration of vehicle (5% EtOH/5% Tween-80), Test Compound, or imipramine (60 mg/kg) by oral gavage 1 hour before the swim test.

Experimental Design

The procedure for the forced swim test in the mouse is similar to that described above for the rat, with some modifications. The cylinder used for the test is a 1 liter beaker (10.5 cm diameter×15 cm height) fill to 800 ml (10 cm depth) of 23–25° C. water. Only one 5-minute swim test is conducted for each mouse, between 1300 and 1700 hours. Drug treatments are administered 30–60 minutes before the 5-minute test period. Following all swim sessions, mice are removed from the cylinders, dried with paper towels and placed in a heated cage for 15 minutes. All test sessions are videotaped using a Sony color video camera and recorder for scoring later.

Behavorial Scoring

The behavior during minutes 2–5 of the test is played back on a TV monitor and scored by the investigator. The total time spent immobile (animal floating with only minimal movements to remain afloat) and mobile (swimming and movements beyond those required to remain afloat) are recorded.

Data Analysis

The forced swim test data (time exhibiting immobility, mobility; seconds) are subjected to a randomized, one-way ANOVA and post hoc tests conducted using the Newman-Keuls test. The data are analyzed using the GraphPad Prism (v2.01) (GraphPad Software, Inc., San Diego, Calif.). All data are presented as means±S.E.M.

Social Interaction Test (SIT)

Rats are allowed to acclimate to the animal care facility for 5 days and are housed singly for 5 days prior to testing. Animals are handled for 5 minutes per day. The design and procedure for the Social Interaction Test is carried out as previously described by Kennett, et al. (1997). On the test day, weight matched pairs of rats (±5%), unfamiliar to each other, are given identical treatments and returned to their home cages. Animals are randomly divided into 5 treatment groups, with 5 pairs per group, and are given one of the following i.p. treatments: Test Compound (10, 30 or 100 mg/kg), vehicle (1 ml/kg) or chlordiazepoxide (5 mg/kg). Dosing is 1 hour prior to testing. Rats are subsequently placed in a white perspex test box or arena (54×37×26 cm), whose floor is divided up into 24 equal squares, for 15 minutes. An air conditioner is used to generate background noise and to keep the room at approximately 74° F. All sessions are videotaped using a JVC camcorder (model GR-SZ1, Elmwood Park, N.J.) with either TDK (HG ultimate brand) or Sony 30 minute videocassettes. All sessions are conducted between 1300–1630 hours. Active social interaction, defined as grooming, sniffing, biting, boxing, wrestling, following and crawling over or under, is scored using a stopwatch (Sportsline model no. 226, 1/100 sec. discriminability) The number of episodes of rearing (animal completely raises up its body on its hind limbs), grooming (licking, biting, scratching of body), and face ishing (i.e. hands are moved repeatedly over face), and number of squares crossed are scored. Passive social interaction (animals are lying beside or on top of each other) is not scored. All behaviors are assessed later by an observer who is blind as to the treatment of each pair. At the end of each test, the box is thoroughly wiped with moistened paper towels.

Animals

Male albino Sprague-Dawley rats (Taconic Farms, N.Y.) are housed in pairs under a 12 hr light dark cycle (lights on at 0700 hrs.) with free access to food and water.

Drug Administration

Test Compound is dissolved in 100% DMSO or 5% lactic acid, v/v (Sigma Chemical Co., St. Louis, Mo.). Chlordiazepoxide (Sigma Chemical Co., St. Louis, Mo.) is dissolved in double distilled water. The vehicle consists of 50% DMSO (v/v) or 100% dimethylacetamide (DMA). All drug solutions are made up 10 minutes prior to injection and the solutions are discarded at the end of the test day. The volume of drug solution administered is 1 ml/kg.

Data Analysis

The social interaction data (time interacting, rearing and squares crossed) are subjected to a randomized, one-way ANOVA and post hoc tests conducted using the Student-Newman-Keuls test. The data are subjected to a test of normality (Shapiro-Wilk test). The data are analyzed using the GBSTAT program, version 6.5 (Dynamics Microsystems, Inc., Silver Spring, Md., 1997). All data are presented as means±S.E.M.

References

American Psychiatric Association (1994) Diagnostic and Statistical Manual of Mental Disorders, Fourth Edition. American Psychiatric Association, Washington, D.C.

American Psychiatric Association (1987) Diagnostic and Statistical Manual of Mental Disorders, Third Edition revised. American Psychiatric Association, Washington, D.C.

Amiranoff, B., et al., (1989) Galanin receptor in the rat pancreatic beta cell line Rin m 5F. Molecular characterization by chemical cross-linking. *J. Biol. Chem.*, 264(34): 20714–20717.

*Asymmetric Synthesis* (1983) Vol: 2–5, Academic Press, Editor Morrison, J.

Bakker, R. A., et al., (2000) Constitutive activity of the histamine H1 receptor reveals inverse agonism of histamine H1 receptor-antagonists. *Eur. J. Pharmacol.*, 387: R5-R7.

Borowsky, B., et al., (1999) Cloning and characterization of the human galanin GALR2 receptor. *Peptides,* 19: 1771–1781.

Bradford, M. M. (1976) A rapid and sensitive method for the quantitation of microgram quantities of protein utilizing the principle of the protein-dye binding. *Anal. Biochem.*, 72: 248–254.

Branchek, T. A., et al., (2000) Galanin receptor subtypes. *Trends in Pharm. Sci.*, 21: 109–116.

Bryant, W. M. III, et al., (1993) *Synthetic Communications,* 23: 1617–1625.

Chen, Y., et al., (1992) Solubilization and molecular characterization of active galanin receptors from rat brain. *Biochemistry,* 31(8): 2415–2422.

Choshi, T., et al., (1997) New developments of carbazole syntheses by thermal dielectrocyclic reactions. *Fukuyama Daigaku Yakugakubu Kenkyu Nenpo,* 15: 1–24.

Coppola, G. M. (1987) *Journal of Heterocyclic Chemistry,* 24: 1249.

Cullen, B. (1987) Use of eukaryotic expression technology in the functional analysis of cloned genes. *Methods Enzymol.,* 152: 685–704.

deLigt, R. A., et al., (2000) Inverse agonism at G protein-coupled receptors: (patho)physiological relevance and implications for drug discovery. *Br. J. Pharmacol.,* 130(1): 1–12.

*Design of Prodrugs,* (1985) Elsevier, editor Bundgaard, H.

De Weille, J. R., et al., (1989) Galanin inhibits dopamine secretion and activates a potassium channel in pheochromocytoma cells. *Brain Res.,* 485: 199–203.

Detke, M. J., et al., (1995) Active behaviors in the rat forced swim test differentially produced by serotonergic and noradrenergic antidepressants. *Psychopharmacology,* 121: 66–72.

Ennis, M. D. and Ghazal, N. B., (1992) The synthesis of (+) and (−)-flesinoxan: Application of enzymatic resolution methodology. *Tetrahedron Lett.,* 33: 6287–6290.

File, S. E. (1985) Animal models for predicting clinical efficacy of anxiolytic drugs: social behaviour. *Neuropsychobiology,* 13: 55–62.

File, S. E. and Pellow, S. (1984) The anxiogenic action of FG 7142 in the social interaction test is reversed by chlordiazepoxide and Ro-15-1788 but not by CGS 8216. *Archs. Int. Pharmacodyn. Ther.,* 271: 198–205.

File, S. E. and Pellow, S. (1983) The anxiogenic action of a convulsant benzodiazepine: reversal by chlordiazepoxide. *Brain Res.,* 278: 370–372.

File, S. E., et al., (1982) The anxiogenic action of benzodiazepine-like antagonists. *Neuropharmacology,* 21: 1033–1037.

File, S. E. (1980) The use of social interaction as a method for detecting anxiolytic activity of chlordiazepoxide-like drugs. *J. Neurosci. Methods,* 2: 219–238.

File, S. E. and Hyde, J. R. G. (1979) A test of anxiety that distinguishes between the actions of benzodiazepines and those of other minor tranquilisers and of stimulants. *Pharmacol. Behav. Biochem.,* 11: 65–69.

File, S. E. and Hyde, J. R. G. (1978) Can social interaction be used to measure anxiety? *Br. J. Pharmacol.,* 62: 19–24.

Fusco, R., et al., (1978) Fischer synthesis of indoles from 2,6-disubstituted arylhydrazones. *Khom. Geterotsikl. Soedin.* 2: 200–216.

Garden, S. J., et al., (1998). *Synthetic Communications,* 28: 1679–1689.

Glover, V. (1998) Function of endogenous monoamine oxidase inhibitors (tribulin). *J. Neural. Transm. Suppl.,* 52: 307–13.

Gopalan, C., et al., (1993) Neurochemical evidence that the inhibitory effect of galanin on tuberoinfundibular dopamine neurons is activity dependent. *Neuroendocrinology,* 58: 287–293.

Green, T. W. and Wuts, P. G. M. (1991) Protection groups in *Organic Synthesis,* second Edition John Wiley & Sons, New York.

Guy, A. P. and Gardner, C. R. (1985) Pharmacological characterisation of a modified social interaction model of anxiety. *Neuropsychobiology,* 13: 194–200.

Harlow, E. and Lane, D. (1999) *Immunoblotting.* In: Barker, P. editor. Using Antibodies: A Laboratory Manual. New York: Cold Spring Harbor Laboratory Press. p 267–309.

Harrison, T. (1996) Saturated nitrogen heterocycles. 3(4): 259–275.

Herrick-Davis, K., et al., (2000) Inverse agonist activity of atypical antipsychotic drugs at human 5-Hydroxytryptamine2C receptors. *J. Pharmacol. Exp. Ther.,* 295(1): 226–32.

Hess, B. A. Jr. and Corbino, S. (1971) *Journal of Heterocyclic Chemistry,* 8: 161.

Hökfelt, T., et al., (1998) Galanin in Ascending Systems. *Annals of the N.Y. Acad. Sci.,* Ed. T. Hokfelt, Tamas Bartfai and J. Crawley p. 252–263.

Iversen, L. (2000) Neurotransmitter transporters: fruitful targets for CNS drug discovery. *Mol. Psychiatry,* 5(4): 357–62.

Jansson, A., et al., (1989) Centrally administered galanin reduces dopamine utilization in the median eminence and increases dopamine utilization in the medial neostriatum of the male rat. *Acta Physiol. Scand.,* 135: 199–200.

Javitch, J. A., et al, (1984) $^3$H-Mazindol binding associated with neuronal dopamine and norepinephrine uptake sites. *Molecular Pharmacology,* 26: 35–44.

Jaques, J., et al., (1981) *Enantiomer, Racemates and Resolutions.* John Wiley & Sons.

Julius, D., et al., (1988) Molecular characterization of a functional cDNA encoding the serotonin 1c receptor. *Science,* 241: 558–564.

Kenakin, T. (1996) The classification of seven transmembrane receptors in recombinant expression systems. *Pharmacol. Rev.,* 48(3): 413–63.

Kennett, G. A., et al., (1997) Anxiolytic-like actions of the selective 5-HT4 receptor antagonist SB-20470-A and SB-20766-A in rats. *Neuropharmacology,* 36(4–5): 707–712.

Kirby, L. G. and Lucki, I. (1997) Interaction between the forced swimming test and fluoxetine treatment on extracellular 5-hydroxytryptamine and 5-hydroxyindoleacetic acid in the rat. *Stress,* 2(4): 251–263.

Katritzky, A. R., (1996) Recent progress in the synthesis of 1,2,3,4-Tetrahydroquinolines. *Tetrahedron,* 52(48): 15031–15070.

Kouznetsov, V. et al., (1998) Some Aspects of Reduced Quinoline chemistry. *J. Heterocycl. Chem.,* 35(4): 761–785.

Leonard B E. (1996) New approaches to the treatment of depression. *J Clin Psychiatry.* 57(4): 26–33.

Lightowler, S., et al., (1994) Anxiolytic-like effect of paroxetine in a rat social interaction test. *Pharmacol. Behav. Biochem.,* 49: 281–285.

Lucki, I. (1997) The forced swimming test as a model for core and component behavioral effects of antidepressant drugs. *Behav. Pharmacol.,* 8: 523–528.

Lutz, M. and Kenakin, T. (1999) *Quantitative Molecular Pharmacology and Informatics in Drug Discovery,* John Wiley & Sons, LTD, West Sussex, England. p. 153.

Misane, I., et al., (1998) Modulation of a 5-HT1A receptor-mediated beavioral response by the neuropeptide galanin. *Ann. N.Y. Acad. Sci.,* 863: 442–444.

Monsma, F. J. Jr., et al., (1993) Cloning and expression of a novel serotonin receptor with high affinity for tricyclic psychotropic drugs. *Mol. Pharmacol.,* 43: 320–327.

Nógrádi, M. (1987) *Stereoselective Synthesis,* VCH, Editor Ebel, H.

Nordstrom, O., et al., (1987) Evidence for an inhibitory effect of the peptide galanin on dopamine release from the rat median eminence. *Neurosci. Lett.,* 73: 21–26.

Owens, M. J. (1997) Neurotransmitter receptor and transporter binding profile of antidepressants and their metabolites. *J. Pharm. Exp. Ther.,* 283: 1305–1322.

Otsuka, S. and Kobayashi, Y. (1964) A radioisotopic assay for monoamine oxidase determinations in human plasma. *Biochem. Pharmacol.,* 13: 995–1006.

Page, M. E., et al., (1999) Serotonergic mediation of the effects of fluoxetine, but not desipramine, in the rat forced swim test. *Psychopharmacology,* 147: 162–167.

Parker, E. M., et al., (1995) Cloning and characterization of the rat GALR1 galanin receptor from Rin14B insulinoma cells. *Mol. Brain Res.,* 34: 179–189.

Paxinos, G. and Watson, C. (1986) The Rat Brain in Stereotaxic Coordinates. San Diego: Academic Press, Inc.

Pindur, U. (1990) Recent developments in the syntheses of carbazole alkaloids. *Chimia* 44(12): 406–412.

Porsolt, R. D. (1981) Behavioral despair. In Enna, S J (ed) *Antidepressants: neurochemical, behavioral and clinical perspectives.* Raven Press, New York, pp. 121–139.

Porsolt, R. D., et al., (1978) Behavioral despair in rats: a new model sensitive to antidepressant treatments. *Eur. J. Pharmacol.,* 47: 379–391.

Porsolt, R. D., et al., (1977) Depression: a new animal model sensitive to antidepressant treatments. *Nature,* 266: 730–732.

Preobrazhenskaya, M. N., et al., (1967) Synthesis of substituted indoles through indolines. *Usp. Khim.* 36(10): 1760–1798.

Razani, H., et al., (1997) 5-HT1A receptor activation: short-term effects on the mRNA expression of the 5-HT1A receptor and galanin in the raphe nuclei. *Neuroreport,* 8(16): 3565–3570

Reneric, J. P. and Lucki, I. (1998) Antidepressant behavioral effects by dual inhibition of monoamine reuptake in the rat forced swim test. *Psychopharmacology,* 136: 190–197.

Rodgers, R. J., et al., (1997) Animal models of anxiety: an ethological perspective. *Braz. J. Med. Biol. Res.,* 30: 289–304.

Servin, A. L., et al., (1987) Identification and molecular characterization of galanin receptor sites in rat brain. *Biochem. Biophys. Res. Commun.,* 144(1): 298–306.

Seutin, V., et al., (1989) Galanin decreases the activity of locus coeruleus neurons in vitro. *Euro. J. Pharmacol.* 164: 373–376.

Smith, K. E., et al., (1998) Cloned human and rat galanin GALR3 receptors Pharmacology and activation of G-protein inwardly rectifying K+channels. *J. Biol. Chem.,* 273(36): 23321–223326.

Sternberger, L. A. (1982) Neurotypy: regional individuality in rat brain detected by immunocytochemistry with monoclonal antibodies. *Proc. Natl. Acad. Sci. USA,* 79: 1326–1330.

Sukhomlinov, A. K. et al., (1987) Acridine: A base for synthesis of pharmaceuticals. *Farm. Zh.* 4: 34–38.

Tatsumi, M., et al., (1997) Pharmacological profile of antidepressants and related compounds at human monoamine transporters. *Eur. J. Pharmacol.,* 340(2–3): 249–258.

Toda, Y., et al., (1999) Application of tyramide signal amplification system to immunohistochemistry: a potent method to localize antigens that are not detectable by ordinary method. *Pathol. Int.,* 49(5): 479–483.

Treit, D. (1985) Animal models for the study of anti-anxiety agents: a review. *Neurosci. Biobehav. Rev.,* 9: 203–222.

Weiss, J. M., et al., (1998) *Annals of the N.Y. Acad. Sci.,* (Ed. T. Hokfelt, Tamas Bartfai and J. Crawley) p. 364–382.

Xu, Z., et al., (1998) Galanin-5-hydroxytryptamine interactions: Electrophysiological, immunohistochemical and in situ hybridization studies on rat dorsal raphe neurons with a note on galanin R1 and R2 receptors. *Neuroscience,* 87: 79–94.

What is claimed is:

1. A compound having the structure:

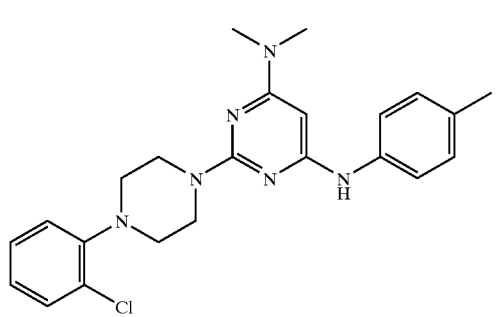

2. A compound having the structure:

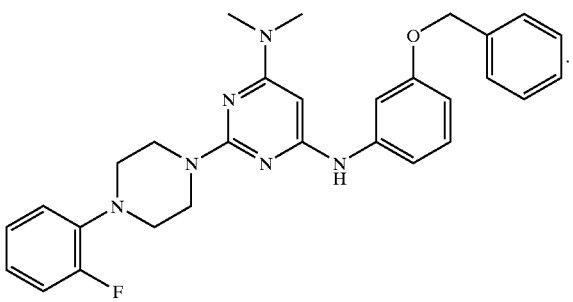

3. A compound having the structure:

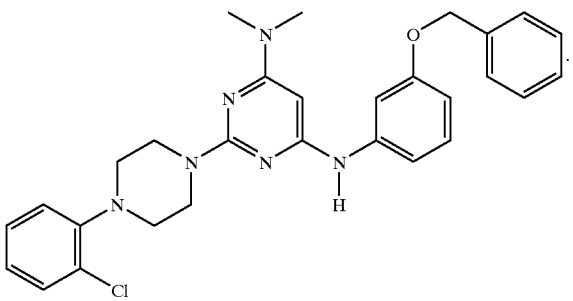

4. A compound having the structure:

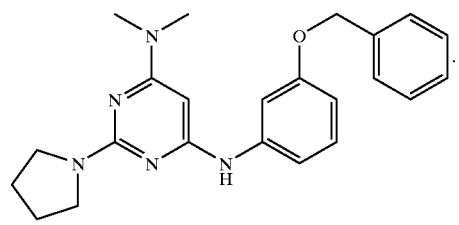

5. A compound having the structure:

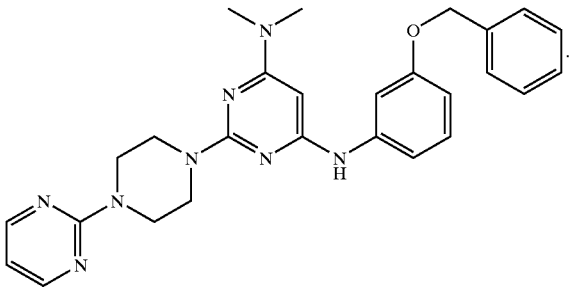

6. A compound having the structure:

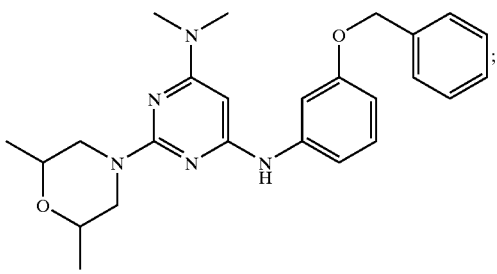

wherein the methyl groups off the morpholine are trans to each other.

7. The compound of claim 6, wherein the compound is enantiomerically pure.

8. A pharmaceutical composition comprising a therapeutically effective amount of the compound of claim 6 and a pharmaceutically acceptable carrier.

9. The pharmaceutical composition of claim 8, wherein the amount of the compound is from about 0.01 mg to about 1000 mg.

10. The pharmaceutical composition of claim 9, wherein the amount of the compound is from about 0.1 mg to about 500 mg.

11. The pharmaceutical composition of claim 10, wherein the amount of the compound is from about 1 mg to about 200 mg.

12. The pharmaceutical composition of claim 11, wherein the amount of the compound is from about 10 mg to about 100 mg.

13. The pharmaceutical composition of claim 12, wherein the carrier is a liquid and the composition is a solution.

14. The pharmaceutical composition of claim 8, wherein the carrier is a solid and the composition is a tablet.

15. The pharmaceutical composition of claim 8, wherein the carrier is a gel and the composition is a suppository.

16. A process of making a pharmaceutical composition comprising admixing a therapeutically effective amount of the compound of claim 6 and a pharmaceutically acceptable carrier.

17. A method of treating a subject suffering from depression, which comprises administering to the subject a dose of the compound of claim 6 effective to treat the subject's depression.

18. A method of treating a subject suffering from anxiety, which comprises administering to the subject a dose of the compound of claim 6 effective to treat the subject's anxiety.

19. The method of claim 17, wherein the therapeutically effective amount is between about 0.01 and about 1000 mg per day.

20. The method of claim 19, wherein the therapeutically effective amount is between about 0.10 and about 500 mg per day.

21. The method of claim 20, wherein the therapeutically effective amount is between about 1.0 and about 200 mg per day.

22. The method of claim 21, wherein the therapeutically effective amount is between about 10 and about 100 mg per day.

23. The method of claim 17, wherein the compound can be administered orally.

24. The method of claim 17, wherein the subject is a vertebrate, a mammal, a canine or a human.

25. The method of claim 17, wherein the compound is administered in combination with food.

* * * * *

UNITED STATES PATENT AND TRADEMARK OFFICE
CERTIFICATE OF CORRECTION

PATENT NO. : 6,936,607 B2
DATED : August 30, 2005
INVENTOR(S) : Packiarajan

It is certified that error appears in the above-identified patent and that said Letters Patent is hereby corrected as shown below:

<u>Title Page,</u>
Item [73], Assignee, "H. Lunobeck A/S, Valby-Copenhagen (DK)" should read
-- H. Lundbeck A/S, Valby-Copenhagen (DK) --.

Signed and Sealed this

Twenty-third Day of May, 2006

JON W. DUDAS
*Director of the United States Patent and Trademark Office*